United States Patent [19]

Change

[11] 4,405,357
[45] Sep. 20, 1983

[54] HERBICIDAL 3-ISOXAZOLIDINONES AND HYDROXAMIC ACIDS

[75] Inventor: Jun H. Chang, Lockport, N.Y.

[73] Assignee: FMC Corporation, Philadelphia, Pa.

[21] Appl. No.: 262,715

[22] Filed: May 11, 1981

Related U.S. Application Data

[63] Continuation-in-part of Ser. No. 155,353, Jun. 2, 1980, abandoned.

[51] Int. Cl.³ .............................................. A01N 43/00
[52] U.S. Cl. ........................................ 71/88; 71/118; 260/500 SH; 260/545 R; 260/453 RW; 548/243; 549/434; 556/417
[58] Field of Search ................... 260/500.5 H, 545 R, 260/453 RW; 71/88, 118; 548/243; 556/417; 549/434

[56] References Cited

U.S. PATENT DOCUMENTS

| | | | |
|---|---|---|---|
| 2,399,118 | 4/1946 | Homeyer | 548/229 |
| 2,437,388 | 3/1948 | Homeyer | 548/229 |
| 2,437,389 | 3/1948 | Homeyer | 548/229 |
| 2,843,585 | 7/1958 | Surrey | 548/229 |
| 2,860,043 | 11/1958 | Bluestone | 71/2.5 |
| 3,007,936 | 11/1961 | Matter et al. | 260/307 |
| 3,264,317 | 8/1966 | Stoffel | 260/307 |
| 3,282,986 | 11/1966 | Kaczka | 260/471 |
| 3,371,106 | 2/1968 | Berliner et al. | 260/453 |
| 3,567,776 | 3/1971 | Krenzer et al. | 260/545 |
| 3,691,234 | 9/1972 | Kiefer et al. | 260/545 R |
| 3,840,596 | 10/1974 | Richter et al. | 260/453 RW |
| 4,062,670 | 12/1977 | Pilgram | 71/88 |
| 4,065,463 | 12/1977 | Beck et al. | 260/307 A |
| 4,207,091 | 6/1980 | Fischer | 71/115 |

FOREIGN PATENT DOCUMENTS

| | | |
|---|---|---|
| 670881 | 4/1966 | Belgium . |
| 1226364 | 3/1965 | Fed. Rep. of Germany . |
| 1044637 | of 1976 | Japan . |
| 1136633 | 12/1968 | United Kingdom ............... 71/88 |
| 1574822 | 9/1980 | United Kingdom . |

OTHER PUBLICATIONS

Geffken, "Archiv der Pharmazie", (1976), vol. 309, No. 5, pp. 413–421.
U.S. Pat. Application Ser. No. 180,053, Aug. 1980, Konz.
Koehetkov, N. K., Khomutov, R. M., Severin, E. S., Karpeiskii, M. Y., Budovskii, E. I., and Erashko, V. I., "Cycloserine and Related Compounds, VIII. Synthesis of 3-Isoxazolidones" *Zhur. Obschei Khim.* 29, 3417–3424 (1959); C.A. 54, 15361f (1960).
Schutyser, J. A. and DeSchryver, F. C., "Photochemistry of Heterocyclic Compounds. Azetidin-2,4-diones" *Chem. Ind. (London)* 1972,465; C.A. 77, 87451j, (1972).
Stamm, H. and Steudle, H., "Nitrones. XI. Isoxazolidine Compound VIII. N-substituted 5-isoxazolidinones by Reformatskii Reaction with Nitrones" *Tetrahedron* 1979, 35 (5), 647–650; C.A. 91, 140751z (1979).

*Primary Examiner*—Anton H. Sutto
*Attorney, Agent, or Firm*—Harrison H. Young, Jr.; H. Robinson Ertelt; Robert L. Andersen

[57] ABSTRACT

Novel 3-isoxazolidinone compounds and novel hydroxamic acid intermediates from which they are prepared exhibit herbicidal activity to grassy and broad-leaf plant species while leaving legumes, especially soybeans, unaffected. The preparation and herbicidal activity of the compounds is exemplified.

36 Claims, No Drawings

HERBICIDAL 3-ISOXAZOLIDINONES AND HYDROXAMIC ACIDS

The present application is a continuation-in-part of U.S. Ser. No. 155,353 filed June 2, 1980, abandoned, the disclosures in which are incorporated herein by reference.

This invention describes novel herbicidal compounds, new herbicidal compositions, and new methods for preventing and destroying undesired plant growth by premergence and postemergence application of the new and useful herbicidal compositions to the locus where control is desired. Effective control of the growth of a variety of both grassy and broad-leaf plant species is obtained. At levels of application which prevent growth of a variety of weeds the compounds of the invention show selectively favorable to legumes, especially to soybeans, and to plants which are vegetatively propagated, especially potatoes. The herbicidal compositions may be applied and utilized by commonly accepted methods.

Oxazole and isoxazole rings carrying one, two, and three carbonyl oxygens have been described in the literature. Some of these have been stated to possess herbicidal activity, for example, a limited class of isoxazolin-5-ones disclosed in U.S. Pat. No. 4,065,463 (Dec. 27, 1977), and isoxazolin-3-ones disclosed in a Derwent Abstract (41047X/22) of Japanese Kokai 44,637/1976 (Apr. 16, 1976). A number of references to isoxazolidine-3-ones have been seen, but none have included assertions of herbicidal activity. Isoxazolidine-3,5-diones were described in U.S. Pat. No. 3,007,936 (Nov. 7, 1961), some of which were stated to have pharmaceutical utility. Oxazolidine-2,4,5-triones disclosed in U.S. Pat. No. 3,264,317 (Aug. 2, 1966) are alleged to have herbicidal activity.

No reference disclosing the isoxazolidin-3-ones of the present invention has been found, and no reference has been found which suggests the outstanding selective herbicidal activity of these compounds.

The present invention provides for the first time disubstituted hydroxamic acids with herbicidal activity, used as intermediates to prepare the novel isoxazolidin-3-ones of the present invention. No reference to these 3-chloro-N-hydroxy-2,2-dimethyl-N-substituted propanamides has been found, and their herbicidal activity has not been previously disclosed.

The herbicidal compounds of this invention have the formula

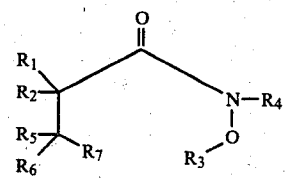

wherein
$R_1$ and $R_2$ are the same or different $C_1$–$C_4$ alkyl; $R_3$ is hydrogen, $C_1$–$C_4$ alkyl, $C_7$–$C_{14}$ aralkyl, pyranyl, tert-butyl-dimethylsilyl, or

in which $R_8$ is alkyl, aryl, amino, alkyl- or arylsubstituted amino, alkoxy, phenoxy, alkylthio, arylthio, halo-substituted alkyl, and any aryl may be halo-, methyl-, methoxy-, nitro-, amino-, or $CF_3$-substituted;
$R_4$ is hydrogen, alkyl, phenyl,

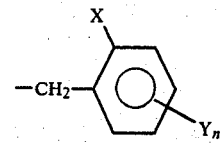

in which X is hydrogen, halogen, $C_1$–$C_4$ alkyl, phenyl, and Y is halogen, —$CF_3$, $C_1$–$C_4$ alkyl, nitro, methoxy, methylenedioxy, and n is 0, 1, or 2;
$R_5$ is hydrogen, halogen, alkyl, aryl, alkoxy, aryloxy, alkylthio, arylthio, amino, alkyl-substituted amino, OH or its derivatives (including but not limited to acetate, benzoate, tosylate, or carbamate), or with $R_1$ forms a ring;
$R_6$ is hydrogen, halogen, alkyl, aryl, alkoxy, aryloxy, alkylthio, arylthio, amino, alkyl-substituted amino, OH or its derivatives (including but not limited to acetate, benzoate, tosylate, carbamate);
$R_7$ is hydrogen, or halogen;
and $R_3$ and $R_7$ may comprise a single carbon-oxygen bond, forming a ring structure.

Preferred compounds of the invention are those in which
$R_1$ and $R_2$ are methyl, ethyl; $R_4$ is

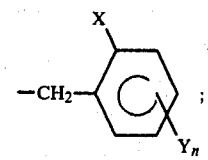

$R_5$ and $R_6$ are hydrogen, chlorine, bromine, methoxy.
Particularly preferred compounds of the invention in which $R_4$ is

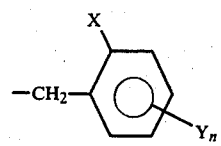

are those in which X is 2-chloro, 2-bromo, 2-fluoro, and Y is 4-chloro, 4-bromo, 4-F, 5-F, and 4,5-methylenedioxy, and n is 0 or 1.

Especially preferred compounds of the invention are those in which $R_1$ and $R_2$ are methyl; $R_3$ and $R_7$ are hydrogen or comprise a single carbon-oxygen bond, forming a ring structure.

Preparation of the compounds of the invention and of intermediates from which they are prepared is described in the following examples. In the descriptions which follow, all temperatures are in degrees centigrade, and reduced pressures are shown in Pascals (Pa); pressures not so designated are pressures normally attainable using a water aspirator.

EXAMPLE 1

3-Chloro-N-(2-chlorophenyl)methyl-N-hydroxy-2,2-dimethylpropanamide

Step A-1 Synthesis of 2-chlorobenzaldoxime

A stirred solution of 250 grams (1.78 moles) of 2-chlorobenzaldehyde in 1235 ml of ethanol was cooled to 20° and 146 grams (2.1 moles) of hydroxylamine hydrochloride was added in one portion. The addition caused the reaction mixture temperature to rise to 30°. The addition of the hydroxylamine hydrochloride was followed by the dropwise addition of a solution of 106.8 grams (2.67 moles) of sodium hydroxide in 320 ml of water. The addition of the sodium hydroxide solution required 30 minutes during which time the reaction mixture temperature rose to 45°. Upon completion of addition the reaction mixture was stirred for 1.5 hours, then was poured into 5500 ml of water. The mixture was stirred for one hour then filtered to collect a white solid; mp 72°–73°.

The solid was dried in a vacuum oven to give 178.3 grams of 2-chlorobenzaldoxime. The nmr and the ir spectra were consistent with the assigned structure.

Step A-2 Synthesis of N-(2-chlorophenylmethyl)hydroxylamine

A stirred solution of 77.8 grams (0.50 mole) of 2-chlorobenzaldoxime and a trace of methyl orange in 700 ml of methanol was cooled to 20°. Solutions of 39 grams (0.62 mole) of sodium cyanoborohydride in 350 ml of methanol and 500 ml of methanolic 2 N hydrochloric acid were added dropwise simultaneously over a 1.5-hour period. During the addition care was taken to keep the reaction mixture at 20° and acidic. Upon completion of addition the reaction mixture was stirred at 20° for 30 minutes, during which time the reaction mixture was kept acidic by the addition of small amounts of methanolic 2 N hydrochloric acid (total amount added—approximately 10 ml). After this the reaction mixture was allowed to warm to ambient temperature where it was stirred for 1.5 hours. The methanol solvent was removed from the reaction mixture under reduced pressure to give a residual solid. The solid was dissolved in 1400 ml of water and the solution made basic with 100 ml of aqueous 6 N potassium hydroxide. A precipitated solid was collected by filtration and washed with 250 ml of water. The dried solid weighed 66.0 grams; mp 70.5°–72.5°.

The water filtrate was extracted with two portions of 250 ml each of methylene chloride. The combined extracts were dried with magnesium sulfate and filtered. The filtrate was concentrated under reduced pressure to give 9.8 grams of solid; mp 70°–72°. The solids were combined and recrystallized from hexane:ethyl acetate (10:1) using decolorizing carbon to give 64.5 grams of N-(2-chlorophenylmethyl)hydroxylamine; mp 71°–73°.

Step B Synthesis of 3-chloro-2,2-dimethylpropionyl chloride

Under an argon atmosphere a stirred solution of 30.0 grams (0.22 mole) of 3-chloro-2,2-dimethylpropionic acid in 100 ml of thionyl chloride was heated under reflux for four hours. After this the reaction mixture was allowed to cool to ambient temperature where it was stirred for 16 hours. The excess thionyl chloride was removed by distillation. The residual oil was distilled under reduced pressure to give 31.1 grams of 3-chloro-2,2-dimethylpropionyl chloride; bp 88°–89°/8 KPa.

The nmr and the ir spectra were consistent with the assigned structure.

Step C Synthesis of 3-chloro-N-(2-chlorophenyl)methyl-N-hydroxy-2,2-dimethylpropanamide Under an argon atmosphere a stirred solution of 10.2 grams (0.065 mole) of N-(2-chlorophenylmethyl)hydroxylamine and 6.1 grams (0.077 mole) of pyridine in 80 ml of methylene chloride was cooled to −10°. A solution of 10.0 grams (0.065 mole) of 3-chloro-2,2-dimethylpropionyl chloride in 20 ml of methylene chloride was added dropwise to the hydroxylamine solution during a 20 minute period. Upon completion of addition the reaction mixture was allowed to warm to ambient temperature where it was stirred for 16 hours. The reaction mixture was diluted with 100 ml of methylene chloride and washed with 100 ml of water, 100 ml of aqueous 10% hydrochloric acid, and finally 100 ml of water. The organic layer was dried with magnesium sulfate and filtered. The filtrate was concentrated under reduced pressure to give a residual oil. The oil was taken up in 25 ml of hexane and cooled in an icewater bath. The resultant solid precipitate was collected by filtration and recrystallized from hexane:ethyl acetate to give 3.7 grams of 3-chloro-N-(2-chlorophenyl)methyl-N-hydroxy-2,2-dimethylpropanamide; mp 108°–110°.

The nmr and the ir spectra were consistent with the assigned structure.

Analysis calc'd for $C_{12}H_{15}Cl_2NO_2$: C 52.19; H 5.47; N 5.07; Found: C 51.90; H 5.18; N 5.07.

EXAMPLE 2

N-(2-chlorophenyl)methyl-N-hydroxy-2,2-dimethylpropanamide

This compound was prepared in the manner of Example 1, Step C, using 6.0 grams (0.05 mole) of trimethylacetyl chloride, 9.5 grams (0.06 mole) of N-(2-chlorophenylmethyl)hydroxylamine (prepared in Example I, Step A), and 14.2 grams (0.18 mole) of pyridine in 60 ml of methylene chloride. The crude product was recrystallized from hexane to give 3.5 grams of N-(2-chlorophenyl)methyl-N-hydroxy-2,2-dimethylpropanamide; mp 100°–102°.

The nmr and the ir spectra were consistent with the assigned structure.

Analysis calc'd for $C_{12}H_{16}ClNO_2$: C 59.62; H 6.67; N 5.79; Found: C 59.78; H 6.38; N 5.87.

EXAMPLE 3

3-Chloro-N-hydroxy-N-phenyl-2,2-dimethylpropanamide

Step A Synthesis of N-phenylhydroxylamine

To a vigorously stirred solution of 61.5 grams (0.50 mole) of nitrobenzene and 31.0 grams (0.58 mole) of ammonium chloride in 1000 ml of water was rapidly added 77.5 grams of zinc dust. The resultant exothermic reaction caused temperature of the reaction mixture to rise to 65°. Upon completion of addition the reaction mixture was stirred for 20 minutes and filtered. The filter cake was washed with 125 ml of hot water. The filtrate was saturated with solid sodium chloride and cooled to 0° in an ice/water-salt bath. A solid precipitate was collected by filtration and washed with hexane to remove unreacted nitrobenzene. The solid was slurried with diethyl ether to remove the product from the sodium chloride. The mixture was dried with magnesium sulfate and filtered. The filtrate was concentrated under reduced pressure to give 32.3 grams of N-phenylhydroxylamine.

Step B Synthesis of 3-chloro-N-hydroxy-N-phenyl-2,2-dimethylpropanamide

Under an argon atmosphere a stirred solution of 10.0 grams (0.065 mole) of 3-chloro-2,2-dimethylpropionyl chloride (prepared in the manner of Example 1, Step B) in 70 ml of methylene chloride was cooled to −70° and 6.1 grams (0.075 mole) of pyridine was added dropwise. A solution of 7.0 grams (0.065 mole) of N-phenylhydroxylamine in 30 ml of methylene chloride was then added dropwise over a 20-minute period. During the addition the reaction mixture temperature rose to −55°. Upon completion of addition the reaction mixture was stirred at −70° to −55° for 30 minutes, then was allowed to warm to ambient temperature where it was stirred for two hours. The reaction mixture was diluted with 100 ml of methylene chloride and washed with 100 ml of water, 100 ml of an aqueous 10% hydrochloric acid solution, and finally with 100 ml of water. The organic layer was dried by standing over magnesium sulfate for 16 hours. The darkened mixture was filtered and the filtrate concentrated under reduced pressure to give a black residue. The residue was slurried with 15 ml of hexane and the insolubles collected by filtration. The insoluble material was recrystallized from hexane/ethyl acetate to give 3.7 grams of 3-chloro-N-hydroxy-N-phenyl-2,2-dimethylpropanamide; mp 120°–121°.

The nmr and the ir spectra were consistent with the assigned structure.

Analysis calc'd for $C_{11}H_{14}ClNO_2$: C 58.02; H 6.20; N 6.15; Found: C 58.30; H 5.99; N 6.19.

EXAMPLE 4

N-(2-bromophenyl)methyl-3-chloro-N-hydroxy-2,2-dimethylpropanamide

Step A-1 Synthesis of 2-bromobenzaldoxime

This compound was prepared in the manner of Example 1, Step A-1 using 25.0 grams (0.135 mole) of 2-bromobenzaldehyde, 18.8 grams (0.270 mole) of hydroxylamine hydrochloride, and 8.1 grams (0.20 mole) of sodium hydroxide in 150 ml of ethanol and 50 ml of water. The yield of 2-bromobenzaldoxime was 26.3 grams; mp 123°–124°.

The nmr and the ir spectra were consistent with the assigned structure.

Step A-2 Synthesis of N-(2-bromophenylmethyl)hydroxylamine

This compound was prepared in the manner of Example 1, Step A-2, using 20.0 grams (0.10 mole) of 2-bromobenzaldoxime, 7.8 grams (0.124 mole) of sodium cyanoborohydride, 20 drops of methyl orange indicator, 112 ml of methanolic 2 N hydrochloric acid, and 170 ml of methanol. The yield of N-(2-bromophenylmethyl)hydroxylamine was 17.7 grams; mp 67°–68°.

The nmr and the ir spectra were consistent with the assigned structure.

A small sample of the product was sublimed (mp 72°–73°) for analytical purposes.

Analysis calc'd for $C_7H_8BrNO$: C 41.61; H 3.99; N 6.93; Found: C 41.50; H 3.93; N 6.97.

Step B Synthesis of N-(2-bromophenyl)methyl-3-chloro-N-hydroxy-2,2-dimethylpropanamide Under an argon atmosphere a stirred solution of 8.8 grams (0.044 mole) of N-(2-bromophenylmethyl)hydroxylamine and 12.0 grams (0.152 mole) of pyridine in 200 ml of methylene chloride was cooled to −10°. The reaction vessel was fitted with a septum and 5.2 grams (0.048 mole) of trimethylchlorosilane was added in small portions from a hypodermic syringe. Upon completion of addition the reaction mixture was stirred at −10° for 30 minutes, then allowed to warm to 0°. At this temperature a solution of 6.7 grams (0.044 mole) of 3-chloro-2,2-dimethylpropionyl chloride (prepared in the manner of Example 1, Step B) in 5 ml of methylene chloride was added dropwise over a 20-minute period. Upon completion of addition the reaction mixture was allowed to warm to ambient temperature where it was stirred for 18 hours. The reaction mixture was poured into a separatory funnel and diluted with 50 ml of methylene chloride. The mixture was washed with 50 ml of water, 50 ml of an aqueous solution saturated with sodium chloride, two portions of 100 ml each of a solution consisting of 1:1—aqueous saturated sodium chloride solution:aqueous 10% hydrochloric acid solution, and finally 50 ml of an aqueous solution saturated with sodium chloride. The organic layer was dried with magnesium sulfate and filtered. The filtrate was concentrated under reduced pressure to give a semi-solid residue. The semi-solid was slurried in 15 ml of hexane. The insoluble material was collected by filtration and recrystallized twice from hexane/ethyl acetate to give 5.7 grams of N-(2-bromophenyl)methyl-3-chloro-N-hydroxy-2,2-dimethylpropanamide; mp 119°–121°.

The nmr and the ir spectra were consistent with the assigned structure.

Analysis calc'd for $C_{12}H_{15}BrClNO_2$: C 44.95; H 4.71; N 4.37; Found: C 44.71; H 4.44; N 4.18.

EXAMPLE 5

3-Chloro-N-hydroxy-2,2-dimethyl-N-(2-methylphenyl)methylpropanamide

Step A-1 Synthesis of 2-methylbenzaldoxime

This compound was prepared in the manner of Example 1, Step A-1, using 50.0 grams (0.416 mole) of 2-methylbenzaldehyde, 57.8 grams (0.832 mole) of hydroxylamine hydrochloride and 25.0 grams (0.624 mole) of sodium hydroxide in 231 ml of ethanol and 155 ml of water. The yield of 2-methylbenzaldoxime was 48.0 grams.

The nmr spectrum was consistent with the assigned structure.

Step A-2 Synthesis of N-(2-methylphenylmethyl)hydroxylamine

This compound was prepared in the manner of Example 1, Step A-2, using 48.0 grams (0.355 mole) of 2-methylbenzaldoxime, 29.0 grams (0.462 mole) of sodium cyanoborohydride, a trace of methyl orange indicator, 396 ml of methanolic 2 N hydrochloric acid, and 750 ml of methanol. The yield of N-(2-methylphenylmethyl)hydroxylamine was 20.2 grams; mp 66°–68.5°.

The nmr and the ir spectra were consistent with the proposed structure.

Analysis calc'd for $C_8H_{11}NO$: C 70.04; H 8.08; N 10.21; Found: C 70.21; H 8.27; N 10.27.

Step B Synthesis of 3-chloro-N-hydroxy-2,2-dimethyl-N-(2-methylphenyl)methylpropanamide This compound was prepared in the manner of Example 4, Step B, using 10.0 grams (0.065 mole) of 3-chloro-2,-2-dimethylpropionyl chloride (prepared in the manner of Example 1, Step B), 8.8 grams (0.065 mole) of N-(2-methylphenylmethyl)hydroxylamine, 7.7 grams (0.071 mole) of trimethylchlorosilane and 17.8 grams (0.226 mole) of pyridine in 205 ml of methylene chloride. The yield of 3-chloro-N-hydroxy-2,2-dimethyl-N-[(2-methylphenyl)methyl]propanamide was 8.5 grams; mp 112°–113°.

The nmr and the ir spectra were consistent with the assigned structure.

Analysis calc'd for $C_{13}H_{18}ClNO_2$: C 61.05; H 7.09; N 5.48; Found: C 61.06; H 7.00; N 5.58.

EXAMPLE 6

3-Chloro-N-hydroxy-2,2-N-trimethylpropanamide

This compound was prepared in the manner of Example 4, Step B, using 12.0 grams (0.077 mole) of 3-chloro-2,-2-dimethylpropionyl chloride (prepared in the manner of Example 1, Step B), 6.5 grams (0.077 mole) of N-methylhydroxylamine hydrochloride, 8.8 grams (0.081 mole) of trimethylchlorosilane and 27.5 grams (0.348 mole) of pyridine in 130 ml of methylene chloride. The yield of 3-chloro-N-hydroxy-2,2-N-trimethylpropanamide was 5.3 grams; mp 54°–57°.

The nmr and the ir spectra were consistent with the proposed structure.

Analysis calc'd for $C_6H_{12}ClNO_2$: C 43.41; H 7.31; N 8.46; Found: C 43.48; H 7.10; N 8.40.

EXAMPLE 7

3-Chloro-N-hydroxy-2,2-dimethyl-N-(phenylmethyl)-propanamide

Step A-1 Synthesis of benzaldoxime

This compound was prepared in the manner of Example 1, Step A-1, using 50.0 grams (0.471 mole) of benzaldehyde, 65.5 grams (0.942 mole) of hydroxylamine hydrochloride, and 27.9 grams (0.698 mole) of sodium hydroxide in 400 ml of ethanol and 110 ml of water. The yield of benzaldoxime was 56.9 grams as an oil.

Step A-2 Synthesis of N-phenylmethylhydroxylamine

This compound was prepared in the manner of Example 1, Step A-2, using 56.9 grams (0.470 mole) of benzaldoxime, 36.5 grams (0.582 mole) of sodium cyanoborohydride, 90 drops of 1-ethyl-2-[3-(1-ethylnaphtho[1,2d]thiazolin-2-ylidene)-2-methylpropenyl]naphtho[1,2d]-thiazolium bromide (a pH indicator-Stainsall ®), 277 ml of methanolic 2 N hydrochloric acid and 800 ml of methanol. The yield of N-phenylmethylhydroxylamine was 20.0 grams; mp 54°–56.5°.

The nmr and the ir spectra were consistent with the assigned structure.

Step B Synthesis of 3-chloro-N-hydroxy-2,2-dimethyl-N-(phenylmethyl)propanamide

This compound was prepared in the manner of Example 4, Step B, using 10.0 grams (0.065 mole) of 3-chloro-2,-2-dimethylpropionyl chloride (prepared in the manner of Example 1, Step B), 8.0 grams (0.065 mole) of N-phenylmethylhydroxylamine, 7.8 grams (0.072 mole) of trimethylchlorosilane, and 17.6 grams (0.223 mole) of pyridine in 200 ml of methylene chloride. The yield of 3-chloro-N-hydroxy-2,2-dimethyl-N-(phenylmethyl)-propanamide was 6.1 grams; mp 90°–92°.

The nmr and the ir spectra were consistent with the assigned structure.

Analysis calc'd for $C_{12}H_{14}ClNO_2$: C 59.62; H 6.67; N 5.80; Found: C 58.63; H 5.93; N 5.56.

EXAMPLE 8

3-Chloro-N-(2,4-dichlorophenylmethyl)-N-hydroxy-2,2-dimethylpropanamide

Step A-1 Synthesis of 2,4-dichlorobenzaldoxime

This compound was prepared in the manner of Example 1, Step A-1, using 50.0 grams (0.286 mole) of 2,4-dichlorobenzaldehyde, 39.7 grams (0.572 mole) of hydroxylamine hydrochloride, and 23.0 grams (0.572 mole) of sodium hydroxide in 245 ml of ethanol and 85 ml of water. The yield of 2,4-dichlorobenzaldoxime was 51.3 grams as a solid.

Step A-2 Synthesis of N-(2,4-dichlorophenylmethyl)-hydroxylamine

This compound was prepared in the manner of Example 1, Step A-2, using 51.3 grams (0.271 mole) of 2,4-dichlorobenzaldoxime, 21.1 grams (0.336 mole) of sodium cyanoborohydride, 1 ml of 1-ethyl-2-[3-(1-ethylnaphtho[1,2d]-thiazolin-2-ylidene)-2-methylpropenyl]-naphtho[1,2d]thiazolium bromide, 157 ml of methanolic 2 N hydrochloric acid and 885 ml of methanol. The yield of N-(2,4-dichlorophenylmethyl)hydroxylamine was 33.7 grams as a solid.

The nmr spectrum was consistent with the assigned structure.

Step B Synthesis of 3-chloro-N-(2,4-dichlorophenyl)-methyl-N-hydroxy-2,2-dimethylpropanamide This compound was prepared in the manner of Example 4, Step B, using 10.0 grams (0.065 mole) of 3-chloro-2,-2-dimethylpropionyl chloride (prepared in the manner of Example 1, Step B), 18.9 grams (0.072 mole) of N-(2,4-dichlorophenylmethyl)hydroxylamine, 11.9 grams (0.107 mole) of trimethylchlorosilane and 27.2 grams (0.344 mole) of pyridine in 200 ml of methylene chloride. The yield of 3-chloro-N-(2,4-dichlorophenyl)-methyl-N-hydroxy-2,2-dimethylpropanamide was 6.9 grams; mp 103°–105.5°.

The nmr and the ir spectra were consistent with the assigned structure.

Analysis calc'd for $C_{12}H_{14}Cl_3NO_2$: C 46.39; H 4.54; N 4.51; Found: C 45.81; H 4.08; N 4.40.

EXAMPLE 9

3-Chloro-N-(2-chlorophenyl)methyl)-N-methoxy-2,2-dimethylpropanamide

Step A-1 Synthesis of N-methoxy-(2-chlorophenyl)-methanimine

This compound was prepared in the manner of Example 1, Step A-1, using 25.0 grams (0.178 mole) of 2-chlorobenzaldehyde, 16.4 grams (0.196 mole) of methoxyamine hydrochloride, and 7.8 grams (0.196 mole) of sodium hydroxide in 300 ml of ethanol. The yield of N-methoxy(2-chlorophenyl)methanimine was 30.8 grams as an oil.

The nmr and the ir spectra were consistent with the assigned structure.

Analysis calc'd for $C_8H_8ClNO$: C 56.64; H 4.76; N 8.26; Found: C 56.60; H 4.84; N 8.22.

Step A-2 Synthesis of N-methoxy-2-chlorophenylmethylamine

This compound was prepared in the manner of Example 1, Step A-2, using 15 grams (0.088 mole) of N-methoxy(2-chlorophenyl)methanimine, 6.8 grams (0.109 mole) of sodium cyanoborohydride, 2 ml of 1-ethyl-2-[3-(1-ethylnaphtho[1,2d]thiazolin-2-ylidene)-2-methylpropenyl]naphtho[1,2d]thiazolium bromide, 51 ml of methanolic 2 N hydrochloric acid and 150 ml of methanol. The yield of N-methoxy-2-chlorophenylmethylamine was 6.8 grams; bp 70°–72°/0.2 KPa.

The nmr and the ir spectrum were consistent with the assigned structure.

Step B Synthesis of 3-chloro-N-(2-chlorophenyl)methyl-N-methoxy-2,2-dimethylpropanamide This compound was prepared in the manner of Example 1, Step C, using 6.2 grams (0.040 mole) of 3-chloro-2,2-dimethylpropionyl chloride (prepared in the manner of Example 1, Step B), 6.8 grams (0.04 mole) of N-methoxy-2-chlorophenylmethylamine and 6.3 grams (0.08 mole) of pyridine in 50 ml of methylene chloride. The yield of 3-chloro-N-(2-chlorophenyl)methyl-N-methoxy-2,2-dimethylpropanamide was 10.3 grams; bp 122°–127°/6.7 Pa.

The nmr and the ir spectra were consistent with the assigned structure.

Analysis calc'd for $C_{13}H_{17}Cl_2NO_2$: C 53.81; H 5.90; N 4.83; Found: C 54.09; H 6.10; N 4.97.

EXAMPLE 10

3,3-Dichloro-N-(2-chlorophenyl)methyl-N-hydroxy-2,2-dimethylpropanamide

Step A Synthesis of 3,3-dichloro-2,2-dimethylpropionyl chloride

This compound was prepared in the manner of Example 1, Step B, using 25.0 grams (0.146 mole) of 3,3-dichloro-2,2-dimethylpropionic acid and 100 ml of thionyl chloride. The yield of 3,3-dichloro-2,2-dimethylpropionyl chloride was 23.4 grams; bp 64°–66°/1.6 KPa.

The ir spectrum was consistent with the assigned structure.

Step B Synthesis of 3,3-dichloro-N-(2-chlorophenyl)methyl-N-hydroxy-2,2-dimethylpropanamide This compound was prepared in the manner of Example 4, Step B, using 10.0 grams (0.053 mole) of 3,3-dichloro-2,2-dimethylpropionyl chloride, 8.3 grams (0.053 mole) of N-(2chlorophenylmethyl)hydroxylamine, 6.3 grams (0.058 mole) of trimethylchlorosilane, and 14.6 grams (0.185 mole) of pyridine in 205 ml of methylene chloride. The yield of 3,3-dichloro-N-(2-chlorophenyl)methyl-N-hydroxy-2,2-dimethylpropanamide was 9.5 grams; mp 136°–138°.

The nmr and the ir spectra were consistent with the assigned structure.

Analysis of $C_{12}H_{14}Cl_3NO_2$: C 46.40; H 4.54; N 4.51; Found: C 46.21; H 4.68; N 4.55.

EXAMPLE 11

3-Chloro-N-(2-fluorophenyl)methyl-N-hydroxy-2,2-dimethylpropanamide

This compound was prepared in the manner of Example 4, Step B, using 10.0 grams (0.065 mole) of 3-chloro-2,-2-dimethylpropionyl chloride (prepared in the manner of Example 1, Step B), 9.1 grams (0.0645 mole) of N-(2-fluorophenylmethyl)hydroxylamine (commercially prepared), 7.7 grams (0.071 mole) of trimethylchlorosilane, and 17.8 grams (0.226 mole) of pyridine in 200 ml of methylene chloride. The yield of 3-chloro-N-(2-fluorophenyl)methyl-N-hydroxy-2,2-dimethylpropanamide was 8.0 grams; mp 110°–112°.

The nmr and the ir spectra were consistent with the assigned structure.

Analysis calc'd for $C_{12}H_{15}ClFNO_2$: C 55.50; H 5.82; N 5.39; Found: C 55.51; H 5.86; N 5.42.

EXAMPLE 12

3-Bromo-N-(2-chlorophenyl)methyl-N-hydroxy-2,2-dimethylpropanamide

Step A Synthesis of 3-hydroxy-2,2-dimethylpropionic acid

To a stirred solution of 8.8 grams (0.219 mole) of sodium hydroxide in 50 ml of water was added 10.0 grams (0.073 mole) of 3-chloro-2,2-dimethylpropionic acid. The resultant solution was heated under reflux for two hours. The reaction mixture was cooled to ambient temperature and acidified with concentrated hydrochloric acid. The mixture was saturated with solid sodium chloride and extracted with three portions of 50 ml each of methylene chloride then with three portions of 50 ml each of diethyl ether. The combined extracts were dried with sodium sulfate and filtered. The filtrate was concentrated under reduced pressure to give 5.9 grams of 3-hydroxy-2,2-dimethylpropionic acid; mp 123°–124°.

The nmr and the ir spectra were consistent with the assigned structure.

Analysis calc'd for $C_5H_{10}O_3$: C 50.84; H 8.53; Found: C 50.40; H 8.26.

Step B Synthesis of 3-bromo-2,2-dimethylpropionic acid

A stirred solution of 4.5 grams (0.038 mole) of 3-hydroxy-2,2-dimethylpropionic acid in 45.0 grams of aqueous 48% hydrobromic acid was heated under reflux for 24 hours. The reaction mixture was cooled to ambient temperature and diluted with 100 ml of saturated aqueous solution of sodium chloride. The mixture was extracted with four portions of 50 ml each of methylene chloride and four portions each of diethyl ether. The combined extracts were washed with two portions of 50 ml each of distilled water then dried with sodium sulfate. The mixture was filtered and the filtrate concentrated under reduced pressure to a residual solid. The solid was recrystallized twice from cold pentane to give 4.0 grams of 3-bromo-2,2-dimethylpropionic acid; mp 46°–48°.

The nmr and the ir spectra were consistent with the assigned structure.

Analysis calc'd for $C_5H_9BrO_2$: C 33.17; H 5.01; Found: C 34.68; H 4.93.

Step C Synthesis of 3-bromo-2,2-dimethylpropionyl chloride

This compound was prepared in the manner of Example 1, Step B.

Step D Synthesis of 3-bromo-N-(2-chlorophenyl)methyl-N-hydroxy-2,2-dimethylpropanamide This compound was prepared in the manner of Example 4, Step B. Solid; mp 102°–105°. The nmr and the ir were consistent with the assigned structure.

Analysis calc'd for $C_{12}H_{15}BrClNO_2$: C 44.95; H 4.72; N 4.37; Found: C 45.64; H 4.76; N 4.46.

EXAMPLE 13

N-benzoyloxy-3-chloro-N-(2-chlorophenyl)methyl-2,2-dimethylpropanamide

A stirred solution of 2.0 grams (0.007 mole) of 3-chloro-N-(2-chlorophenyl)methyl-N-hydroxy-2,2-dimethylpropanamide (prepared in Example 1) in 25 ml of methylene chloride was placed under an argon atmosphere and cooled to 0° C. To this was added 0.98 gram (0.007 mole) of benzoyl chloride in 5 ml of methylene chloride followed by 0.63 gram (0.008 mole) of pyridine. Upon completion of addition the reaction mixture was heated under reflux for 16 hours. The reaction mixture was diluted with methylene chloride and washed with 100 ml of water, 100 ml of aqueous 10% hydrochloric acid and finally 100 ml of an aqueous solution saturated with sodium bicarbonate. The organic layer was dried with magnesium sulfate and filtered. The filtrate was concentrated under reduced pressure to give a residual oil. The oil was subjected to column chromatography on silica gel. The appropriate fraction was concentrated under reduced pressure to give 4.1 grams of solid. The solid was recrystallized from ethyl acetate/cyclohexane. A precipitate was collected by filtration; mp 117°–120°. Nuclear magnetic resonance spectroscopy indicated the precipitate to be benzoic acid. The mother liquor was concentrated under reduced pressure and the residue redissolved in 60 ml of methylene chloride. The solution was washed with five portions of 20 ml each of an aqueous solution saturated with sodium bicarbonate. The organic layer was dried with sodium sulfate and filtered. The filtrate was concentrated under reduced pressure to give an oil residue. Volatiles were removed from the oil under reduced pressure using a short-path distilling system. There remained as a residue 1.0 gram of N-benzoyloxy-3-chloro-N-(2-chlorophenyl)methyl-2,2-dimethylpropanamide.

The nmr and the ir spectra were consistent with the assigned structure.

Analysis calc'd for $C_{19}H_{19}NCl_2O_3$: C 60.01; H 5.04; N 3.68; Found: C 60.01; H 4.76; N 3.92.

EXAMPLE 14

N-acetoxy-3-chloro-N-(2-chlorophenyl)methyl-2,2-dimethylpropanamide

This compound was prepared in the manner of Example 13, using 0.86 g (0.011 mole) acetyl chloride. Liquid; bp 70°–74°/7 Pa. The nmr and the ir spectra were consistent with the assigned structure.

Analysis calc'd for $C_{14}H_{17}Cl_2NO_3$: C 52.85; H 5.38; N 4.40; Found: C 52.99; H 5.31; N 4.20.

EXAMPLE 15

N-(chloroacetoxy)-3-chloro-N-(2-chlorophenyl)methyl-2,2-dimethylpropanamide

This compound was prepared in the manner of Example 13, using 4.0 g (0.014 mole) of 3-chloro-N-(2-chlorophenyl)methyl-N-hydroxy-2,2-dimethylpropanamide (prepared in Example 1), 1.6 g (0.014 mole) of chloroacetyl chloride, and 1.2 g (0.015 mole) of pyridine, in 50 ml toluene. The product was a liquid, of which nmr and ir spectra were consistent with the assigned structure.

Analysis calc'd for $C_{14}H_{16}NCl_3O_3$: C 47.68; H 4.57; N 3.97; Found: C 47.85; H 4.30; N 3.86.

EXAMPLE 16

2-(2-Chlorophenyl)methyl-4,4-dimethyl-3-isoxazolidinone

To a stirred solution of 6.3 grams (0.023 mole) of 3-chloro-N-(2-chlorophenyl)methyl-N-hydroxy-2,2-dimethylpropanamide (prepared in Example 1) in 45 ml of methanol was added dropwise a solution of 1.5 grams (0.023 mole) potassium hydroxide (85% pure) in 25 ml of methanol. The addition required 15 minutes during which time the reaction mixture temperature rose from 24° to 32°. Upon completion of addition the reaction mixture was stirred for 18 hours at ambient temperature. The reaction mixture was filtered to remove by-product potassium chloride. The filtrate was poured into 500 ml of ice-water. The mixture was extracted with two portions of 250 ml each of methylene chloride. The combined extracts were dried with magnesium sulfate and filtered. The filtrate was concentrated under reduced pressure to give 5.2 grams of 2-(2-chlorophenyl)methyl-4,4-dimethyl-3-isoxazolidinone as an oil.

The nmr and the ir spectra were consistent with the assigned structure.

Analysis calc'd for $C_{12}H_{14}ClNO_2$: C 60.13; H 5.89; N 5.84; Found: C 60.01; H 5.60; N 6.09.

EXAMPLE 17

4,4-Dimethyl-2-phenyl-3-isoxazolidinone

This compound was prepared in the manner of Example 16, using 2.5 grams (0.11 mole) of 3-chloro-N-hydroxy-N-phenyl-2,2-dimethylpropanamide (prepared in Example 3), and 0.62 gram (0.011 mole) of potassium hydroxide in 40 ml of methanol. The yield of 4,4-dimethyl-2-phenyl-3-isoxazolidinone was 1.2 grams as an oil.

The nmr and the ir spectra were consistent with the assigned structure.

Analysis calc'd for $C_{11}H_{13}NO_2$: C 69.09; H 6.85; N 7.33; Found: C 68.80; H 6.72; N 7.26.

EXAMPLE 18

2-(2-Bromophenyl)methyl-4,4-dimethyl-3-isoxazolidinone

This compound was prepared in the manner of Example 16, using 3.7 grams (0.012 mole) of N-(2-bromophenyl)methyl-3-chloro-N-hydroxy-2,2-dimethylpropanamide (prepared in Example 4), and 0.75 gram (0.012 mole) of 85% pure potassium hydroxide in 40 ml of methanol. The yield of 2-(2-bromophenyl)methyl-4,4-dimethyl-3-isoxazolidinone was 3.0 grams as an oil.

The nmr and the ir spectra were consistent with the assigned structure.

Analysis calc'd for $C_{12}H_{14}BrNO_2$: C 50.72; H 4.97; N 4.93; Found: C 51.01; H 4.68; N 5.16.

EXAMPLE 19

4,4-Dimethyl-2-(2-methylphenyl)methyl-3-isoxazolidinone

This compound was prepared in the manner of Example 16, using 5.1 grams (0.020 mole) of 3-chloro-N-hydroxy-2,2-dimethyl-N-(2-methylphenyl)methylpropanamide (prepared in Example 5), and 1.3 grams (0.020 mole) of 85% pure potassium hydroxide in 60 ml of methanol. The yield of 4,4-dimethyl-2-(2-methylphenyl)methyl-3-isoxazolidinone was 3.9 grams as an oil.

The nmr and the ir spectra were consistent with the assigned structure.

Analysis calc'd for $C_{13}H_{17}NO_2$: C 71.20; H 7.82; N 6.39; Found: C 71.10; H 7.55; N 6.31.

EXAMPLE 20

2,4,4-Trimethyl-3-isoxazolidinone

This compound was prepared in the manner of Example 16, using 3.0 grams (0.018 mole) of 3-chloro-N-hydroxy-2,2-N-trimethylpropanamide (prepared in Example 6), and 1.2 grams (0.018 mole) of 85% pure potassium hydroxide in 60 ml of methanol. The yield of 2,4,4-trimethyl-3-isoxazolidinone was 2.2 grams as an oil.

The nmr and the ir spectra were consistent with the assigned structure.

Analysis calc'd for $C_6H_{11}NO_2$: C 55.79; H 8.59; N 10.85; Found: C 54.70; H 8.28; N 10.87.

EXAMPLE 21

4,4-Dimethyl-2-phenylmethyl-3-isoxazolidinone

This compound was prepared in the manner of Example 16, using 3.0 grams (0.013 mole) of 3-chloro-N-hydroxy-2,2-dimethyl-N-(phenylmethyl)propanamide (prepared in Example 7), and 0.8 gram (0.013 mole) of 85% pure potassium hydroxide in 60 ml of methanol. The yield of 4,4-dimethyl-2-phenylmethyl-3-isoxazolidinone was 1.7 grams; bp 64°/7 Pa.

The nmr and the ir spectra were consistent with the assigned structure.

Analysis calc'd for $C_{12}H_{15}NO_2$: C 70.22; H 7.34; N 6.83; Found: C 70.38; H 7.60; N 7.05.

EXAMPLE 22

2-(2,4-Dichlorophenyl)methyl-4,4-dimethyl-3-isoxazolidinone

This compound was prepared in the manner of Example 16, using 4.0 grams (0.013 mole) of 3-chloro-N-(2,4-dichlorophenyl)methyl-N-hydroxy-2,2-dimethylpropanamide (prepared in Example 8), and 0.86 gram (0.013 mole) of 85% pure potassium hydroxide in 80 ml of methanol. The yield of 2-(2,4-dichlorophenyl)methyl-4,4-dimethyl-3-isoxazolidinone was 2.4 grams as an oil.

The nmr and the ir spectra were consistent with the assigned structure.

Analysis calc'd for $C_{12}H_{13}Cl_2NO_2$: C 52.55; H 4.78; N 5.14; Found: C 52.56; H 4.80; N 5.01.

EXAMPLE 23

(A)

5-Chloro-2-(2-chlorophenyl)methyl-4,4-dimethyl-3-isoxazolidinone and (B)

2-(2-Chlorophenyl)methyl-5-methoxy-4,4-dimethyl-3-isoxazolidinone

These compounds were prepared in the manner of Example 16, using 7.7 grams (0.025 mole) of 3,3-dichloro-N-(2-chlorophenyl)methyl-N-hydroxy-2,2-dimethylpropanamide (prepared in Example 10) and 1.6 grams (0.025 mole) of 85% pure potassium hydroxide in 70 ml of methanol. Thin layer chromatographic analysis of the reaction mixture on silica gel using 20% ethyl acetate in hexane as an eluent indicated that the reaction mixture was a two-component mixture. The crude reaction mixture was subjected to column chromatography on silica gel using 15% ethyl acetate in heptane. Initial fractions from the chromatography were combined to give 1.7 grams of 5-chloro-2-(2-chlorophenyl)methyl-4,4-dimethyl-3-isoxazolidinone as an oil.

The nmr and the ir spectra were consistent with the assigned structure.

Analysis calc'd for $C_{12}H_{13}Cl_2NO_2$: C 52.57; H 4.78; N 5.11; Found: C 52.39; H 4.56; N 5.20.

The latter fractions from the chromatography were combined to give 1.2 grams of 2-(2-chlorophenyl)methyl-5-methoxy-4,4-dimethyl-3-isoxazolidinone as an oil.

The nmr and the ir spectra were consistent with the assigned structure.

Analysis calc'd for $C_{13}H_{16}ClNO_3$: C 57.89; H 5.98; N 5.19; Found: C 57.64; H 6.13; N 5.04.

EXAMPLE 24

2-(2-Fluorophenyl)methyl-4,4-dimethyl-3-isoxazolidinone

This compound was prepared in the manner of Example 16, using 5.0 grams (0.019 mole) of 3-chloro-N-(2-fluorophenyl)methyl-N-hydroxy-2,2-dimethylpropanamide (prepared in Example 11) and 1.3 grams (0.019 mole) of 85% pure potassium hydroxide in 65 ml of methanol. The yield of 2-(2-fluorophenyl)methyl-4,4-dimethyl-3-isoxazolidinone was 3.9 grams as an oil.

The nmr and the ir spectra were consistent with the assigned structure.

Analysis calc'd for $C_{12}H_{14}FNO_2$: C 64.56; H 6.32; N 6.27; Found: C 64.41; H 6.17; N 6.37.

EXAMPLE 25

N-[(2-Chlorophenyl)methyl]-N,3-dihydroxy-2,2-dimethylpropanamide

To a stirred solution of 3.0 grams (0.025 mole) of 3-hydroxy-2,2-dimethylpropionic acid (Example 12, Step A) and 3.9 grams (0.025 mole) of N-(2-chlorophenyl)methyl hydroxylamine (Example 1, Step A-2) in 65 ml of ethanol was added dropwise a solution of 5.2 grams (0.025 mole) of dicyclohexylcarbodiimide in 25 ml of chloroform. Upon completion of addition the reaction mixture was stirred at ambient temperature for 60 hours. The reaction mixture was concentrated under reduced pressure to give a residual solid. The solid was recrystallized from ethanol, then from ethanol-water to give a solid; mp 229°-230°. The filtrates from the recrystallizations were combined and concentrated under high vacuum to give a residual oil. The residual oil was subjected to column chromatography. Elution was accomplished using 4:1—cyclohexane:ethyl acetate. The appropriate fraction was concentrated under reduced pressure to give a solid. The solid was recrystallized from ethyl acetatehexane to give 0.51 gram of N-[(2-chlorophenyl)methyl]-N,3-dihydroxy-2,2-dimethylpropanamide; mp 130°-132°. The solid was recrystallized a second time from ethyl acetate-cyclohexane to raise the mp to 131°-132°.

The nmr spectrum was consistent with the assigned structure.

Analysis calc'd for $C_{12}H_{16}ClNO_3$: C 55.93; H 6.26; N 5.43; Found: C 58.84; H 6.90; N 6.68.

EXAMPLE 26

3-Chloro-N-[(2-chlorophenyl)methyl]-2,2-dimethyl-N-(methylaminocarbonyloxy)propanamide Under an argon atmosphere a solution of 4.5 grams (0.016 mole) of 3-chloro-N-[(2-chlorophenyl)methyl]-N-hydroxy-2,2-dimethylpropanamide (Example 1) and 1.3 grams (0.016 mole) of pyridine in 5 ml of anhydrous tetrahydrofuran was prepared. To this stirred solution was added dropwise 4.6 grams (0.082 mole) of methyl isocyanate. Upon completion of addition the reaction mixture was stirred at ambient temperature for 60 hours. The reaction mixture was diluted with 100 ml of diethyl ether and washed with three 50-ml portions of water, then with two 50-ml portions of an aqueous solution saturated with sodium bicarbonate. The organic layer was dried with magnesium sulfate and filtered. The filtrate was concentrated under reduced pressure to give a solid residue. The solid was recrystallized from hexane-ethyl acetate to give 3.5 grams of 3-chloro-N-[(2-chlorophenyl)methyl]-2,2-dimethyl-N-(methylaminocarbonyloxy)propanamide; mp 91°–93°.

The nmr and the ir spectra were consistent with the assigned structure.

Analysis calc'd for $C_{14}H_{18}Cl_2N_2O_3$: C 50.46; H 5.44; N 8.41; Found: C 50.70; H 5.40; N 8.36.

EXAMPLE 27

3-Chloro-N-[(2-chlorophenyl)methyl]-N-[(2-tetrahydropyranyl)oxy]-2,2-dimethylpropanamide A suspension of 6.0 grams (0.022 mole) of 3-chloro-N-[(2-chlorophenyl)methyl]-N-hydroxy-2,2-dimethylpropanamide (Example 1) and a catalytic amount of p-toluenesulfonic acid in 30 ml of methylene chloride was stirred at ambient temperature while a solution of 3.7 grams (0.043 mole) of dihydropyran in 5 ml of methylene chloride was added dropwise during a five minute period. Upon completion of addition the reaction mixture was stirred at ambient temperature for two hours. Gas chromatographic analysis of the reaction mixture indicated unreacted propanamide, and additional quantity of p-toluenesulfonic acid was added and the reaction mixture was stirred for 18 hours. A second gas chromatographic analysis of the reaction mixture indicated the unreacted propanamide was still present. The mixture was diluted with 100 ml of methylene chloride and washed with three 100-ml portions of water. The organic layer was dried with magnesium sulfate and filtered. The filtrate was concentrated under reduced pressure to give an oil residue. A sample of the oil was taken up in hot hexane and the solution allowed to cool. A black oil dropped out of the solution. The hexane was decanted from the black oil. Additional oil dropped from the solution and the hexane was again decanted away. The hexane was cooled and a small amount of white solid precipitate was collected by filtration. The solid was unreacted propanamide. The hexane filtrate was concentrated to give a viscous oil residue. The remainder of the oil from the original reaction mixture was dissolved in methylene chloride then dispersed in 12 grams of silica gel. The mixture was placed on a chromatographic column of silica gel and eluted with 20% ethyl acetate in heptane. The appropriate fractions were combined to give 2.7 grams of clear oil residue. The oil was dissolved in 10 ml of 15% ethyl acetate in heptane and placed on a second chromatographic column of silica gel. Elution was accomplished with 15% ethyl acetate in heptane. The appropriate fractions were combined and concentrated under reduced pressure to give 0.6 grams of 3-chloro-N-[(2-chlorophenyl)methyl]-N-[(2-tetrahydropyranyl)oxy]-2,2-dimethylpropanamide as an oil.

The nmr spectrum was consistent with the assigned structure.

Analysis calc'd for $C_{17}H_{23}Cl_2NO_3$: C 56.67; H 6.43; N 3.89; Found: C 55.86; H 6.26; N 3.55.

EXAMPLE 28

3-Chloro-N-[(2-chlorophenyl)methyl]-2,2-dimethyl-N-[dimethyl(1,1-dimethylethyl)silyloxy]propanamide Step A Synthesis of [(2-chlorophenyl)methyl]-[dimethyl(1,1-dimethylethyl)silyloxy]amine A stirred solution of 10.0 grams (0.063 mole) of N-(2-chlorophenyl)methylhydroxylamine (Example 1, Step A-2) and 12.9 grams (0.19 mole) of imidazole in 50 ml of dry dimethylformamide was cooled in an ice-water bath. To this stirred solution was added dropwise during a 20 minute period 10.6 grams (0.07 mole) of tert-butyldimethylsilyl chloride in 25 ml of dry dimethylformamide. During the addition the reaction mixture temperature was maintained at 5°. Upon completion of addition the reaction mixture was allowed to warm to ambient temperature at which it was stirred for 18 hours. Most of the dimethylformamide was removed from the reaction mixture under water aspirator pressure. The residue was taken up in 300 ml of methylene chloride and washed with three 100-ml portions of water. The organic layer was dried with magnesium sulfate and filtered. The filtrate was concentrated under reduced pressure to give on cooling a semi-solid residue. A sample of the semi-solid was slurried with hexane and the insolubles collected by filtration. The filtrate was concentrated to give an oil residue. The above procedure was repeated on the remainder of the semi-solid using 75 ml of hexane. The hexane filtrate was concentrated under reduced pressure to give an oil residue. The oil was distilled under reduced pressure to give 10.2 grams of [(2-chlorophenyl)methyl]-[dimethyl(1,1-dimethylethyl)silyloxy]amine; bp 88°–89°/0.7 Pa.

The nmr and the ir spectra were consistent with the assigned structure. Analysis calc'd for $C_{13}H_{22}ClNOSi$: C 57.43; H 8.16; N 5.15; Found: C 57.57; H 7.90; N 5.30.

Step B Synthesis of 3-chloro-N-[(2-chlorophenyl)methyl]-2,2-dimethyl-N-[dimethyl-(1,1-dimethylethyl)silyloxy]propanamide A stirred solution of 6.5 grams (0.024 mole) of [(2-chlorophenyl)methyl]-[dimethyl(1,1-dimethyl)silyloxy]amine and 3.8 grams (0.048 mole) of pyridine in 60 ml of dry methylene chloride was cooled in an ice-water bath and 3.7 grams (0.024 mole) of 3-chloro-2,2-dimethylpropionyl chloride (Example 1, Step B) in 5 ml of dry methylene chloride was added dropwise during a 10 minute period while the temperature of the reaction mixture was maintained below 5°. Upon completion of addition the reaction mixture was allowed to warm to ambient temperature where it was stirred for 18 hours. The reaction mixture was diluted with 100 ml of methylene chloride and washed with two 75-ml portions of water. The organic layer was dried with magnesium sulfate and filtered. The filtrate was evaporated under reduced pressure to give an oil residue. Volatiles were removed from the oil by distillation at 50°–70°/0.7 Pa. using a shortpath distilling system. The pot residue was dispersed in 10 grams of silica gel and placed on a chromatographic column of silica gel. Elution was accomplished with 10% ethyl acetate in heptane. The appropriate fractions were combined and concentrated under reduced pressure to give 1.6 grams of 3-chloro-N-[(2-chlorophenyl)methyl]-2,2-dimethyl-N-[dimethyl(1,1-dimethylethyl)silyloxy]propanamide as an oil.

The nmr and the ir spectra were consistent with the assigned structure.

Analysis calc'd for $C_{18}H_{29}Cl_2NO_2Si$: C 55.37; H 7.49; N 3.59; Found: C 56.06; H 7.55; N 3.55.

EXAMPLE 29

3-Acetoxy-N-[(2-chlorophenoxy)methyl]-N-hydroxy-2,2-dimethylpropanamide

Step A Synthesis of methyl 3-hydroxy-2,2-dimethylpropionate

To a stirred solution of 30.0 grams (0.22 mole) of 3-chloro-2,2-dimethylpropionic acid in 100 ml of absolute methanol was added dropwise 35.6 grams (0.66 mole) of a methanolic solution 25% in sodium methoxide. The exothermic reaction caused the reaction mixture temperature to rise to 40°. Upon completion of addition the reaction mixture was heated at reflux for 4 hours, then cooled to ambient temperature where it was stirred for one hour. The reaction mixture was acidified with concentrated hydrochloric acid and 150 ml of water was added. The mixture was extracted with four portions of 100 ml each of methylene chloride. The combined extracts were dried with magnesium sulfate and filtered. The filtrate was concentrated under reduced pressure to give 20.8 grams of methyl 3-hydroxy-2,2-dimethylpropionate as an oil.

The nmr and the ir spectra were consistent with the assigned structure.

Step B Synthesis of methyl 3-acetoxy-2,2-dimethylpropionate as an intermediate

Under an argon atmosphere a stirred solution of 10.0 grams (0.076 mole) of methyl 3-hydroxy-2,2-dimethylpropionate and 6.6 grams (0.083 mole) of pyridine in 40 ml of dry methylene chloride was cooled to 0°. To this 6.0 grams (0.076 mole) of acetyl chloride was added dropwise. Upon completion of addition the reaction mixture was allowed to warm to ambient temperature where it was stirred for 18 hours. The reaction mixture was washed with 50 ml of water, two portions of 50 ml each of an aqueous solution of 5% hydrochloric acid, and finally, 50 ml of water. The organic layer was dried with magnesium sulfate and filtered. The filtrate was concentrated under reduced pressure to give an oil residue. The oil was distilled under reduced pressure to give 8.0 grams of methyl 3-acetoxy-2,2-dimethylpropionate; bp 85°–90°/33 Pa.

The nmr and the ir spectra were consistent with the assigned structure.

Analysis calc'd for $C_8H_{14}O$: C 55.16; H 8.10; Found: C 55.17; H 7.92.

Step C Synthesis of 3-acetoxy-2,2-dimethylpropionic acid

To a stirred solution of 4.0 grams (0.023 mole) of methyl 3-acetoxy-2,2-dimethylpropionate in 50 ml of carbon tetrachloride under an argon atmosphere was added slowly via a syringe 9.2 grams (0.046 mole) of iodotrimethylsilane. Upon completion of addition the reaction mixture was stirred at ambient temperature for 60 hours. The reaction mixture was then heated at 50° for 1.5 hours, and at 65° for 18 hours. Nuclear magnetic resonance spectroscopy indicated the reaction had not gone to completion. The reaction mixture was heated at 65° for six days, then poured into 100 ml water. The mixture was stirred for 20 minutes and the carbon tetrachloride layer separated. The water layer was extracted with three portions of 50 ml each of methylene chloride. The methylene chloride extracts and the carbon tetrachloride layer were combined. The combination was dried with magnesium sulfate and filtered. The filtrate was concentrated under reduced pressure to give a semi-solid residue. The semi-solid was dissolved in hot ethyl acetate and treated with decolorizing charcoal. The mixture was filtered and the filtrate concentrated under reduced pressure to give a solid residue. The solid was recrystallized from hexane to give 1.5 grams of 3-acetoxy-2,2-dimethylpropionic acid; mp 56°–59°.

The nmr and the ir spectra were consistent with the assigned structure.

Analysis calc'd for $C_7H_{12}O_4$: C 62.59; H 7.55; Found: C 62.45; H 7.66.

Step D Synthesis of 3-acetoxy-2,2-dimethylpropionyl chloride

Under an argon atmosphere a stirred solution of 1.2 grams (0.008 mole) of 3-acetoxy-2,2-dimethylpropionic acid in 30 ml of toluene was heated to 80° and a solution of 1.9 grams (0.015 mole) of oxalyl chloride in 20 ml of toluene was added dropwise. Upon completion of addition the reaction mixture was heated at 80° for 18 hours. The reaction mixture was concentrated under reduced pressure to give 1.3 grams of 3-acetoxy-2,2-dimethylpropionyl chloride as an oil.

The ir spectrum was consistent with the assigned structure.

Step E Synthesis of 3-acetoxy-N-[(2-chlorophenyl)methyl]-N-hydroxy-2,2-dimethylpropanamide This compound was prepared in the manner of Example 4, Step B, using 1.3 grams (0.008 mole) of 3-acetoxy-2,2-dimethylpropionyl chloride, 1.8 grams (0.011 mole) of N-(2-chlorophenyl)methylhydroxylamine, 1.4 grams (0.012 mole) of trimethylchlorosilane and 2.7 grams (0.034 mole) of pyridine in 100 ml of methylene chloride. The yield of 3-acetoxy-N-[(2-chlorophenyl)methyl]-N-hydroxy-2,2-dimethylpropanamide was 1.1 grams; mp 78°–80°.

The nmr and the ir spectra were consistent with the assigned structure.

Analysis calc'd for $C_{14}H_{18}ClNO_4$: C 56.10; H 6.05; N 4.67; Found: C 56.08; H 6.17; N 4.93.

EXAMPLE 30

2-[(2-Chloro-4-fluorophenyl)methyl]-4,4-dimethyl-3-isoxazolidinone

Step A Synthesis of 3-chloro-N-hydroxy-2,2-dimethylpropanamide

A stirred solution of 28.0 grams (0.40 mole) of hydroxylamine hydrochloride in 60 ml of water was cooled to 0° and a solution of 16.0 grams (0.40 mole) of sodium hydroxide in 40 ml of water was added dropwise while maintaining the temperature of the reaction mixture at 0°–5°. Upon completion of addition 31.0 grams (0.20 mole) of 3-chloro-2,2-dimethylpropionyl chloride was added dropwise during a 45-minute period while maintaining the temperature of the reaction mixture at −3° to −5°. Upon completion of addition the reaction mixture was maintained at 5° for one hour, then was allowed to warm to ambient temperature where it was stirred for 16 hours. A white solid precipitate was collected by filtration and air-dried. The dried solid was recrystallized from ethanol-water to give 12.4 grams of 3-chloro-N-hydroxy-2,2-dimethylpropanamide; mp 148°–151°, decomposes.

The nmr and the ir spectra were consistent with the assigned structure.

Step B Synthesis of 4,4-dimethyl-3-isoxazolidinone

To a stirred solution of 3.9 grams (0.026 mole) of 3-chloro-N-hydroxy-2,2-dimethylpropanamide in 35 ml of methanol was added dropwise a solution of 3.4 grams (0.062 mole) of 85% pure potassium hydroxide in 15 ml of methanol. The resulting reaction was slightly exothermic. Upon completion of addition the reaction mixture was allowed to cool to ambient temperature where it was stirred for 5 hours. The reaction mixture was diluted with 50 ml of water and extracted with 30 ml of methylene chloride. The aqueous layer was acidified then cooled in an ice bath. The mixture was extracted with eight potions of 50 ml each of methylene chloride. The combined extracts were dried with magnesium sulfate and filtered. The filtrate was concentrated under reduced pressure to give 2.7 grams of 4,4-dimethyl-3-isoxazolidinone.

The ir was consistent with the assigned structure.

Step C Synthesis of 2-[(2-chloro-4-fluorophenyl)methyl]-4,4-dimethyl-3-isoxazolidinone A solution of 0.52 grams (0.005 mole) of 4,4-dimethyl-3-isoxazolidinone, 1.0 gram (0.005 mole) of (2-chloro-4-fluorophenyl)methyl bromide and 0.62 gram (0.005 mole) of potassium carbonate in 40 ml of dimethylformamide was stirred at ambient temperature for 18 hours. The dimethylformamide was removed under high vacuum with mild heat. The residue was extracted with methylene chloride. The extract was filtered and dried with sodium sulfate. The mixture was refiltered and the filtrate concentrated under reduced pressure to give an oil residue. The residue was slurried in warm hexane and a solid was removed by filtration. The filtrate was concentrated under reduced pressure to give 0.39 gram of 2-[(2-chloro-4-fluorophenyl)methyl]-4,4-dimethyl-3-isoxazolidinone as an oil.

The nmr spectrum was consistent with the assigned structure.

Analysis calc'd for $C_{12}H_{13}ClFNO_2$: C 55.93; H 5.08; N 5.44; Found: C 55.55; H 5.04; L N 5.33.

EXAMPLE 31

2-[(2-Chloro-5-fluorophenyl)methyl]-4,4-dimethyl-3-isoxazolidinone

This compound was prepared in the manner of Example 30, using 1.16 grams (0.01 mole) of 4,4-dimethyl-3-isoxazolidinone, 2.26 grams (0.01 mole) of (2-chloro-5-fluorophenyl)methyl bromide and 1.40 grams (0.01 mole) of potassium carbonate in 30 ml of acetonitrile. The yield of 2-[(2-chloro-5-fluorophenyl)methyl]-4,4-dimethyl-3-isoxazolidinone was 0.4 gram as an oil.

Analysis calc'd for $C_{12}H_{13}ClFNO_3$: C 55.93; H 5.08; N 5.44; Found: C 55.89; H 4.92; N 5.37.

EXAMPLE 32

2-[(2,4,5-Trichlorophenyl)methyl]-4,4-dimethyl-3-isoxazolidinone

To a stirred suspension of 1.9 grams (0.029 mole) of crushed 85% pure potassium hydroxide and 1.7 grams (0.005 mole) of tetrabutylammonium bromide in 20 ml of tetrahydrofuran was added dropwise a solution of 3.0 grams (0.026 mole) of 4,4-dimethyl-3-isoxazolidinone (Example 30, Step B) and 7.1 grams (0.026 mole) of (2,4,5-trichlorophenyl)methyl bromide in 50 ml of tetrahydrofuran. The addition required one hour. Upon completion of addition the reaction mixture was stirred at ambient temperature for 1.5 hours and then filtered. The filtrate was diluted with 150 ml of methylene chloride and washed with three 75-ml portions of water. The organic layer was dried with magnesium sulfate and filtered. The filtrate was concentrated under reduced pressure to give an oil residue. The oil was subjected to column chromatography on silica gel. Elution was accomplished using 10% ethyl acetate in heptane. The appropriate fractions were combined and concentrated under reduced pressure to give 1.6 grams of 2-[(2,4,5-trichlorophenyl)methyl]-4,4-dimethyl-3-isoxazolidinone as an oil.

The nmr and the ir spectra were consistent with the assigned structure.

Analysis calc'd for $C_{12}H_{12}Cl_3NO_2$: C 46.70; H 3.92; N 4.54; Found: C 46.86; H 3.86; N 4.59.

EXAMPLE 33

2-[(2-Chloro-6-fluorophenyl)methyl]-4,4-dimethyl-3-isoxazolidinone

To a stirred suspension of 3.6 grams (0.026 mole) of potassium carbonate and 0.14 gram (0.0005 mole) of 1,4,7,10,13,16-hexaoxacyclooctadecane in 50 ml of acetonitrile was added dropwise a solution of 3.0 grams (0.026 mole) of 4,4-dimethyl-3-isoxazolidinone (Example 30, Step B) and 4.7 grams (0.025 mole) of (2-chloro-6-fluorophenyl)methyl chloride in 25 ml of acetonitrile. The complete addition required 30 minutes. Upon completion of addition the reaction mixture was stirred at ambient temperature for 18 hours, and then filtered. The filtrate was diluted with 200 ml of methylene chloride and washed with three 100-ml portions of water. The organic layer was dried with magnesium sulfate and filtered. The filtrate was concentrated under reduced pressure to give an oil residue. The oil solidified and was recrystallized from petroleum ether to give 3.0 grams of 2-[(2-chloro-6-fluorophenyl)methyl]-4,4-dimethyl-3-isoxazolidinone; mp 49°–51°.

The nmr and the ir spectra were consistent with the assigned structure.

Analysis calc'd for $C_{12}H_{13}ClFNO_3$: C 55.93; H 5.08; N 5.44; Found: C 55.65; H 5.17; N 5.25.

EXAMPLE 34

2-[(2-Chlorophenyl)methyl]-5-ethoxy-4,4-dimethyl-3-isoxazolidinone

To a stirred solution of 3.0 grams (0.011 mole) of 5-chloro-2-[(2-chlorophenyl)methyl]-4,4-dimethyl-3-isoxazolidinone (Example 23 (A)) in 30 ml of absolute ethanol was added dropwise 1.2 grams (0.012 mole) of triethylamine. Upon completion of addition the reaction mixture was heated under reflux for 18 hours; thin layer chromatography of the reaction mixture indicated no reaction had taken place. The reaction mixture was cooled, 0.74 gram (1 equiv.) of sodium ethoxide was added, and the reaction mixture was stirred at ambient temperature for two hours; again thin layer chromatography on the reaction mixture indicated that no reaction had taken place. The reaction mixture was filtered and diluted with 150 ml of methylene chloride. The mixture was washed with two 100-ml portions of water. The organic layer was dried with magnesium sulfate and filtered. The filtrate was concentrated under reduced pressure to give an oil residue. The oil was distilled at 80°/3.3 Pa. using a short-path distilling system. Nuclear magnetic resonance spectroscopy indicated 83% of the distillate to be the desired product. The distillate was subjected to column chromatography on silica gel, using 20% ethyl acetate in heptane for elution. The appropriate fractions were combined and concentrated under reduced pressure to give 1.3 grams of 2-[(2-chlorophenyl)methyl]-5-ethoxy-4,4-dimethyl-3-isoxazolidinone as an oil.

The nmr and the ir spectra were consistent with the assigned structure.

Analysis calc'd for $C_{14}H_{18}ClNO_3$: C59.26; H 6.39; N 4.94; Found: C 59.61; H 6.57; N 4.72.

EXAMPLE 35

(A)
2-[(2-Chlorophenyl)methyl]-4,4-dimethyl-5-phenylamino-3-isoxazolidinone

(B)
2-[(2-Chlorophenyl)methyl]-5-hydroxy-4,4-dimethyl-3-isoxazolidinone

To a stirred solution of 2.6 grams (0.009 mole) of 5-chloro-2-[(2-chlorophenyl)methyl]-4,4-dimethyl-3-isoxazolidinone (Example 23(A)) in 25 ml of tetrahydrofuran was added dropwise to a solution of 1.8 grams (0.019 mole) of aniline in 5 ml of tetrahydrofuran. Upon completion of addition the reaction mixture was heated under reflux for 4 hours; thin layer chromatography of the reaction mixture indicated the presence of starting 5-chloro compound. The reaction mixture was heated under reflux for an additional 60 hours; thin layer chromatography of the mixture again indicated the 5-chloro starting material to be present. The tetrahydrofuran solvent was removed by evaporation under reduced pressure and 0.9 gram (1 equiv.) of aniline in 20 ml of dimethylformamide was added. The solution was heated at 110°–120° for six hours, and was allowed to cool to ambient temperature where it was stirred for 18 hours. The reaction mixture was poured into 100 ml of water and extracted with three 50-ml portions of methylene chloride. The combined extracts were washed with two 50-ml portions of an aqueous solution of 5% hydrochloric acid. The organic layer was dried with magnesium sulfate and filtered. The filtrate was concentrated under reduced pressure to give an oil residue. The residue was subjected to column chromatography on silica gel using 30% ethyl acetate in heptane. The appropriate fractions were combined and concentrated under reduced pressure to give 1.8 grams of 2-[(2-chlorophenyl)methyl]-4,4-dimethyl-5-phenylamino-3-isoxazolidinone; mp 99°–101°.

The nmr spectrum was consistent with the assigned structure.

Analysis calc'd for $C_{18}H_{19}ClN_2O_2$: C 65.35; H 5.79; N 8.47; Found: C 65.63; H 5.93; N 8.43.

Other fractions were combined and concentrated under reduced pressure to give 0.2 gram of 2-[(2-chlorophenyl)methyl]-5-hydroxy-4,4-dimethyl-3-isoxazolidinone; mp 122°–126°.

The nmr and the ir spectra were consistent with the assigned structure.

Analysis calc'd for $C_{12}H_{14}ClNO_3$: C 57.47; H 5.84; N 5.38; Found: C 57.29; H 5.71; N 5.56.

The methods exemplified above were used to prepare the following additional compounds of the invention. Structures of each were confirmed by nuclear magnetic resonance or infrared spectral analysis, or both; elemental analyses for carbon, hydrogen, and nitrogen conformed to expected values satisfactorily.

Example 36. 3-Chloro—N—[(2-chlorophenyl)methyl]-2,2-dimethyl-N—[(phenylamino)carbonyloxy]-propanamide; mp 166–169°.

Example 37. 3-Chloro—N—[(2-chlorophenyl)methyl]-2,2-dimethyl-N—(phenoxycarbonylloxy)propanamide; mp 105–107°.

Example 38. 3-Chloro—N—[(2-chlorophenyl)methyl]-N—ethoxycarbonyloxy-2,2-dimethylpropanamide; liquid, analysis found: C 51.48, H 5.49, N 4.31.

Example 39. N—Benzoyloxy—3,3-dichloro-N—[(2-chlorophenyl)methyl]-2,2-dimethylpropanamide; mp 93–94°.

Example 40. N—(2-Bromophenyl)methyl]-3,3-dichloro-N—hydroxy-2,2-dimethylpropanamide; mp 147–149°.

Example 41. 3-Chloro—N—[(2-chlorophenyl)methyl]-N—(4-nitrobenzoyloxy)-2,2-dimethylpropanamide; mp 103–106°.

Example 42. 3-Chloro—N—[(2-chlorophenyl)methyl]-2,2-dimethyl-N—[(2-methylphenyl)carbonyloxy]propanamide; liquid, analysis found: C 61.49, H 5.35, N 3.12.

Example 43. 3-Chloro—N—dichloroacetoxy-N—[(2-chlorophenyl)methyl]-2,2-dimethylpropanamide; mp 73–76°.

Example 44. 3-Chloro—N—[(2-chlorophenyl)methyl]-2,2-dimethyl-N—[(4-methylphenyl)sulfonyloxy]propanamide, mp 66–68°.

Example 45. 3-Chloro—N—[(2-chlorophenyl)methyl]-2,2-dimethyl-N—[(1,1-dimethylethyl)carbonyloxy]-propanamide; liquid, analysis found: C 56.57, H 6.31, N 3.74.

Example 46. 3-Chloro—N—[(2-chlorophenyl)methyl]-2,2-dimethyl-N—(ethylthiocarbonyloxy)propanamide; liquid, analysis found: C 53.24, H 4.70, N 6.37.

Example 47. 3-Chloro—N—[(2,2,2-trichloroethoxy)carconyloxy]-N—[(2-chlorophenyl)methyl]-2,3-dimethylpropanamide; mp 89–91°.

Example 48. 3-Chloro—N—[(2-chlorophenyl)aminocarbonyloxy]-N—[(2-chlorophenyl)methyl]-2,2-dimethylpropanamide; mp 115–117°.

Example 49. 3-Chloro—N—[(4-chlorophenyl)aminocarbonyloxy]-N—[(2-chlorophenyl)methyl]-2,2-dimethylpropanamide; mp 180–182°.

Example 50. 3-Chloro—N—[(2-chlorophenyl)methyl]-2,2-dimethyl-N—(phenylmethoxy)propanamide; liquid, analysis found: C 62.27, H 5.50, N 3.84.

Example 51. 3-Chloro—N—(2-chloro-1-oxopropoxy)-N—[(2-chlorophenyl)methyl]-2,2-dimethylpropanamide; liquid analysis found: C 49.34, H 4.69, N 3.81.

Example 52. 3-Chloro—N—[(2,4-dichlorophenoxy)acetoxy]-N—[(2-chlorophenyl)methyl]-2,2-dimethylpropanamide; liquid, analysis found: C 50.96, H 4.31 N 2.77.

Example 53. 3-Chloro—N—[(2-chlorophenyl)methyl]-2,2-dimethyl]-N—[(3-trifluoromethyl)benzoyloxy]propanamide; liquid, analysis found: C 53.37, H 4.05, N 2.98.

Example 54. 3-Chloro—N—[(2-chlorophenyl)methyl]-2,2-dimethyl-N—[(4-methylphenyl)aminocarbonyloxy)-propanamide; mp 177–180°.

Example 55. 3-Chloro—N—[(2-chlorophenyl)methyl]-N—[(3,4-dichlorophenyl)aminocarbonyloxy]-2,2-dimethylpropanamide; mp 153–155°.

Example 56. 3-Chloro—N—(3-chloro-2,2-dimethyl-1-oxopropoxy)-N—[(2-chlorophenyl)methyl]-2,2-dimethylpropanamide; liquid, analysis found: C 51.71, H 5.43, N 3.48.

Example 57. 3-Bromo—N—[(2-bromophenyl)methyl]-N—hydroxy-2,2-dimethylpropanamide; mp 108–110°.

Example 58. 3-Chloro—N—[(2-chlorophenyl)methyl]-N—[(2-fluorophenyl)aminocarbonyloxy]-2,2-dimethylpropanamide; mp 121–123°.

Example 59. 3-Chloro—N—[(2-chlorophenyl)methyl]-N—[(4-methoxyphenyl)aminocarbonyloxy]-2,2-dimethylpropanamide mp 139–141°.

Example 60. 3-Chloro—N—[(2-chlorophenyl)methyl]-N—[(3-trifluoromethylphenyl)aminocarbonyloxy]-2,2-dimethylpropanamide; mp 120–123°.

Example 61. 3-Bromo—N—[(2-chlorophenyl)methyl]-N—(methylaminocarbonyloxy)-2,2-dimethylpropan- mp 79–82°.

Example 62. 3-Bromo—N—(chloroacetoxy)-N—[(2-chlorophenylmethyl]-2,2-dimethylpropanamide; liquid, analysis found: C 42.50, H 4.07, N 3.56.

Example 63. 3-Chloro—N—[(2,5-dichloro-3-(formylamino)-benzoyl]oxy-N—[(2-chlorophenyl)methyl]-2,2-dimethylpropanamide; mp 118–122°.

Example 64. 3-Bromo—N—[(2-bromophenyl)methyl]-N—chloroacetoxy-2,2-dimethylpropanamide; liquid, analysis found: C 37.80, H 3.60, N 3.10.

Example 65. 3-Bromo—N—[(2-bromophenyl)methyl]-N—(methylcarbonyloxy)-2,2-dimethylpropanamide; mp 98–100°.

-continued

| | |
|---|---|
| Example 66. | 3-Bromo—N—[(2-bromophenyl)methyl]-N—[(2-chlorophenyl)aminocarbonyloxy]-2,2-dimethylamide; mp 112–114°. |
| Example 67. | 2-[(2-Chlorophenyl)methyl]-N—hydroxy-2,2-dimethyl-3-methylthiopropanamide; liquid, analysis found: C 54.42, H 6.32, N 4.69. |
| Example 68. | 3-(Phenylcarbonyloxy)-N—[(2-chlorophenyl)methyl]-N—hydroxy-2,2-dimethylpropanamide; mp 101–103°. |
| Example 69. | 2-[(4-Chlorophenyl)methyl]-4,4-dimethyl-3-isoxazolidinone; mp 78–81°. |
| Example 70. | 2-[(3,4-Dichlorophenyl)methyl]-4,4-dimethyl-3-isoxazolidinone; mp 68–69°. |
| Example 71. | 2-[(Chlorophenyl)methyl]-4,4-dimethyl-3-isoxazolidinone-5-ylacetate; liquid, analysis found: C 56.27, H 5.18, N 4.61. |
| Example 72. | 2-[(2-Chlorophenyl)methyl]-4,4-dimethyl-3-isoxazolidinone-5-ylbenzoate; liquid, analysis found: C 65.17, H 4.99, N 3.53. |
| Example 73. | 2-[(2-Chlorophenyl)methyl]-4,4-dimethyl-3-isoxazolidinone-5-yldichloroacetate; mp 67–70°. |
| Example 74. | 2-[(2-Chlorophenyl)methyl]-4,4-dimethyl-3-isoxazolidinone-5-ylphenylcarbamate; mp 147–150°. |
| Example 75. | 2-[(2-Chlorophenyl)methyl]-4,4-dimethyl-3-isoxazolidinone-5-ylmethylcarbamate; mp 135–138°. |
| Example 76. | 2-[(2-Chloro-4-cyanophenyl)methyl]-4,4-dimethyl-3-isoxazolidinone; mp 160–162°. |
| Example 77. | 2-[(2-Chloro-5-methoxyphenyl)methyl]-4,4-dimethyl-3-isoxazolidinone; liquid, analysis found: C 57.75, H 5.63, N 4.98. |
| Example 78. | 2-[(2-Chloro-4-methoxyphenyl)methyl]-4,4-dimethyl-3-isoxazolidinone; liquid, analysis found: C 57.21, H 5.95, N 5.03. |
| Example 79. | 2-[(2,4-Difluorophenyl)methyl]-4,4-dimethyl-3-isoxazolidinone; liquid, analysis found: C 58.80, H 5.64, N 5.93. |
| Example 80. | 2-[(4-Bromo-2-chlorophenyl)methyl]-4,4-dimethyl-3-isoxazolidinone; mp 73–76°. |
| Example 81. | 2-[(2-Bromo-4-fluorophenyl)methyl]-4,4-dimethyl-3-isoxazolidinone; liquid, analysis found: C 47.05, H 4.35, N 4.48. |
| Example 82. | 2-[(6-Chloro-1,3-benzodioxol-5-yl)methyl]-4,4-dimethyl-3-isoxazolidinone; mp 88–90°. |
| Example 83. | 2-[(2-Chlorophenyl)methyl]-4,4-dimethyl-5-phenoxy-3-isoxazolidinone; liquid, analysis found: C 65.09, H 5.70, N 4.08. |
| Example 84. | 2-[(2-Chlorophenyl)methyl]-4,4-dimethyl-5-(1-methylethoxy)-3-isoxazolidinone; bp 90° 0.67 Pa. |
| Example 85. | 2-[(2-Chlorophenyl)methyl]-4,4-dimethyl-5-(phenylmethoxy)-3-isoxazolidinone; mp 80–82°. |
| Example 86. | 2-[(2-Bromophenyl)methyl]-5-chloro-4,4-dimethyl-3-isoxazolidinone; bp 80–85°/0.67 Pa. |
| Example 87. | 2-[(2,5-Dichlorophenyl)methyl]-4,4-dimethyl-3-isoxazolidinone; liquid, analysis found: C 54.79, H 4.51, N 3.20. |
| Example 88. | 2-[(2-Chlorophenyl)methyl]-4,4-dimethyl-5-propoxy-3-isoxazolidinone; bp 80°/3.3 Pa. |
| Example 89. | 2-[(2-Chlorophenyl)methyl]-4,4-dimethyl-5-(2-propenyloxy)-3-isoxazolidinone; liquid, analysis found: C 60.86, H 6.35, N 4.49. |
| Example 90. | 2-[(2-Chlorophenyl)methyl]-4,4-dimethyl-5-(2-propynyloxy)-3-isoxazolidinone; mp 75–76°. |
| Example 91. | 2-[(2-Chlorophenyl)methyl]-4,4-dimethyl-5-(2-methoxyethoxy)-3-isoxazolidinone; liquid, analysis found: C 57.70, H 6.43, N 4.15. |
| Example 92. | 2-[(4-Fluoro-2-iodophenyl)methyl]-4,4-dimethyl-3-isoxazolidinone; liquid, analysis found: C 41.40, H 3.70, N 3.92. |
| Example 93. | 2-[(2-Chlorophenyl)methyl]-5-cyclopentoxy-4,4-dimethyl-3-isoxazolidinone; mp 39–43°. |
| Example 94. | 2-[(2-Chlorophenyl)methyl]-4,4-dimethyl-5-(4-nitrophenoxy)-3-isoxazolidinone; mp 95–98°. |
| Example 95. | 2-[(2-Chlorophenyl)methyl]-5-cyclopropylmethoxy-4,4-dimethyl-3-isoxazolidinone; liquid, analysis found: C 61.47, H 6.57, N 4.44. |
| Example 96. | 2-[(2-Bromophenyl)methyl]-4,4-dimethyl-5-(2-propynoxy)-3-isoxazolidinone; liquid, analysis found: C 53.70, H 4.85, N 3.94. |
| Example 97. | 2-[(2-Chlorophenyl)methyl]-5-(3-butynoxy)-4,4-dimethyl-3-isoxazolidinone; mp 52.5–54°. |
| Example 98. | 2-[(2-Chlorophenyl)methyl]-5-(2-butynoxy)-4,4-dimethyl-3-isoxazolidinone; liquid, analysis found: C 62.15, H 5.79, N 4.46. |
| Example 99. | 2-[(2-Chlorophenyl)methyl]-5-(2-butenoxy)-4,4-dimethyl-3-isoxazolidinone; liquid, analysis found: C 61.97, H 6.31, N 4.41. |
| Example 100. | 2-[(2-Chlorophenyl)methyl]-5-pentoxy-4,4-dimethyl-3-isoxazolidinone; liquid, analysis found: C 62.90, H 7.81, N 4.58. |
| Example 101. | 2-[(2-Chlorophenyl)methyl]-5-hexoxy-4,4-dimethyl-3-isoxazolidinone; liquid, analysis found: C 63.33, H 7.90, N 4.22. |
| Example 102. | 2-[(2-Chlorophenyl)methyl]-5-(1-methylpropoxy)-4,4-dimethyl-3-isoxazolidinone; liquid, analysis found: C 61.39, H 7.27, N 4.70. |
| Example 103. | 2-[(2-Chlorophenyl)methyl]-5-(3-methyl-3-butenoxy)-4,4-dimethyl-3-isoxazolidinone; liquid, analysis found: C 63.18, H 7.09, N 4.05. |
| Example 104. | 2-[(2-Chlorophenyl)methyl]-5-butoxy-4,4-dimethyl-3-isoxazolidinone; liquid, analysis found: C 61.64, H 7.13, N 4.53. |
| Example 105. | 2-[(2-Bromo-5-fluorophenyl)methyl]-4,4-dimethyl-3-isoxazolidinone; liquid, analysis found: C 47.51, H 4.15, N 4.50. |
| Example 106. | 2-[(2-Chlorophenyl)methyl]-4,4-dimethyl-3-isoxazolidinthione; mp 55–57°. |

BIOLOGICAL EVALUATION

The test species used in demonstrating the herbicidal activity of compounds of this invention were lima bean (*Phaseolus limensis*), wild oat (*Avena fatua*), barnyard grass (*Echinochloa crusgalli*), green foxtail (*Sertaria viridis*), velvetleaf (*Abutilon theophrastri*), tomato (*Lycopersicon esculentum*), field bindweed (*Convolvulus arvensis*), soybean (*Glycine max*), sorghum (*Sorghum vulgare*), wild mustard (*Brassica kaber*), johnsongrass (*Sorghum halepense*), cocklebur (*Xanthium pensylvanicum*), small white morningglory (*Ipomoea lacunosa*), purple nutsedge (*Cyperus rotundus*), peanut (*Arachis hypogaea*), cotton (*Gossypium hirsutum*), wild buckwheat (*Polygonum convolvulus*), hemp sesbania (*Sesbania exaltata*), yellow nutsedge (*Cyperus esculentus*).

For the preemergence tests, seeds of the test species were planted in 15×20×8-cm flats containing approximately a 5-cm depth of sandy loam soil. Prior to seeding, the rows were marked by pressing a wooden template onto the soil surface. After sowing, a fungicidal treatment was sprinkled onto the seeds, and a thin layer of soil (approximately 1.0 cm) was applied to the surface of the flat. The spray solutions containing the compounds of the invention were then applied directly to the soil as aqueous acetone solutions at rates equivalent to 4.00 kilograms active ingredient per hectare and submultiples thereof (2.00 kg/ha, 1.00 kg/ha, 0.50 kg/ha) and at a volume equivalent to 750 liters/hectare.

Nutsedge plants for the test were grown in pots containing viable tubers of purple nutsedge or yellow nutsedge planted at a depth of 2.5 cm. These plantings were also treated with the herbicide of the invention.

The test plants were maintained in a greenhouse and watered regularly on the soil surface for two to three weeks, at which time phytotoxicity was observed and recorded. Results are shown in Table 1, and in Table 3.

For postemergence tests, seeds of plant species were seeded in the flats as for preemergence tests, covered with a thin layer (approximately 1.0 cm) of soil, and placed in the greenhouse. They were watered regularly, until the first trifoliate leaves of the lima beans were unfolding (10 to 14 days), at which time the spray solutions containing the compounds of the invention were applied to the plants as aqueous acetone solutions at a rate equivalent to 8.00 kilograms active ingredient per hectare. The treated plants were maintained in the greenhouse and watered regularly for an additional 10 to 14 days, after which the phytotoxicity was observed and recorded. Results are shown in Table 2.

The characteristic phytotoxic effects of the compounds are chlorosis and stunting. Under conditions of the evaluation reported in Table 1 a wide variety of both grassy and broadleaved weeds were controlled at a rate of 1.0 kg/ha, a rate at which crop survival was good for soybeans. For soybeans crop survival was good at a rate of 2.0 kg/ha, a treatment rate which gave excellent control of many of the weed species tested. Results with soybean and representative weeds recorded in Table 3 further illustrate this selectivity.

White potato (*Solanum tuberosum*) was planted from seed pieces in pots at a depth of approximately 1.5 cm and the soil was treated after planting with the compound of Example 1 at rates of 0.25, 0.50, 1.0, 2.0, and 4.0 kg/hectare. These test plants were maintained in a greenhouse and watered regularly on the soil surface. No significant reduction in vigor was observed, and there was no noticeable effect on root growth six weeks after application. Minor signs of chlorosis and stunting were observed at the 2.0 and 4.0 kg/ha levels of application; signs of chlorosis at 0.50 and 1.0 kg/ha levels observed two-to-three weeks after application were outgrown after four weeks. The results show potato to be a tolerant crop.

For herbicidal application the active 3-isoxazolidinones and hydroxamic acid intermediates of this invention will not ordinarily be applied in undiluted form, but will be diluted or extended with an agriculturally acceptable, relatively inert material, here called a carrier, which may be liquid or solid. Thus the compounds of this invention may be utilized in diverse formulations prepared from agricultural adjuvants and agricultural carriers to give the herbicidal compositions contemplated herein. The herbicidal compositions contain between about 0.01% and 95% active ingredient together with between about 4% and 98.5% agriculturally acceptable carrier and between about 1% and 15% surface active agent by weight. As is well-known in the art, the formulation and mode of application of a toxicant may affect the activity of the material in a given application. Thus, a compound of this invention may be formulated as an emulsifiable concentrate, as a granule of relatively large particle size, as a wettable powder, as a solution, or as any of several other known types of formulations, depending on the desired mode of application.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other non-volatile organic solvents. For example, a useful emulsifiable concentrate formulation, designated "4EC" because it contains four pounds of active ingredient per gallon of concentrate (0.479 kg/liter), contains 53.01 parts of 2-(2-chlorophenyl)-methyl-4,4-dimethyl-3-isoxazolidinone, 6.0 parts of a blend of alkylnaphthalenesulfonate and polyoxyethylene ethers as emulsifiers, 1.0 part of epoxidized soybean oil as stabilizer, and as solvent 39.99 parts of petroleum distillate having a high flash-point.

Granular formulations are particularly useful for aerial distribution. Useful granular formulations may be of several types. Impregnated granules are those wherein the active ingredient is applied to large particles of an absorbent carrier, such as an attapulgite or kaolin clay, corncobs, expanded mica, normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for preemergence herbicides, are in the form of finely divided particles which disperse readily in water or other dispersants. The wettable powder is ultimately applied to the soil as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface active agents, many of which are available in commerce.

The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant growth regulators, fertilizers, and other agricultural chemicals. In applying the active compounds of this invention, whether formulated alone or with other agricultural chemicals, an effective amount and concentration of active ingredient are of course employed. The amount constituting an effective amount is variable, depending on a number of factors such as the type of soil, the expected pattern or rainfall or irrigation, the plant species to be controlled, and the crop, if any, to be grown. Generally, a uniform application of between 0.1 and 9 kilograms per hectare will be employed, for example, 0.25 to 4.00 kilograms per hectare.

It is apparent that various modifications may be made in the formulation and application of the novel compounds of this invention, without departing from the inventive concept herein, as defined in the following claims.

TABLE 1

Preemergence Herbicidal Activity of Certain Hydroxamic Acid Derivatives

| Cpd. of Ex. | Plant Species | Rate of Application - kg/ha | | | | | | | | | | |
|---|---|---|---|---|---|---|---|---|---|---|---|---|
| | | 0.500 | | | 1.000 | | | 2.000 | | | 4.000 | | |
| | | V | K | F | V | K | F | V | K | F | V | K | F |
| 1 | Lima Bean | 3 | 0 | 2 | 3 | 0 | 9 | 2 | 20 | 9 | 1 | 80 | 9 |
| | Wild Oat | 0 | 100 | 0 | 0 | 100 | 0 | 0 | 100 | 0 | 0 | 100 | 0 |
| | Barnyardgrass | 0 | 100 | 0 | 0 | 100 | 0 | 0 | 100 | 0 | 0 | 100 | 0 |
| | Green Foxtail | 0 | 100 | 0 | 0 | 100 | 0 | 0 | 100 | 0 | 0 | 100 | 0 |
| | Velvetleaf | 0 | 100 | 0 | 0 | 100 | 0 | 0 | 100 | 0 | 0 | 100 | 0 |
| | Tomato | 2 | 0 | 9 | 2 | 70 | 9 | 1 | 95 | 9 | 0 | 100 | 0 |
| | Field Bindweed | 0 | 100 | 0 | 3 | 90 | 2 | 0 | 100 | 0 | 0 | 100 | 0 |
| | Soybean | 5 | 0 | 0 | 5 | 0 | 0 | 4 | 0 | 9 | 3 | 0 | 9 |
| | Sorghum | 0 | 100 | 0 | 0 | 100 | 0 | 0 | 100 | 0 | 0 | 100 | 0 |
| | Wild Mustard | 2 | 60 | 9 | 2 | 90 | 9 | 0 | 100 | 0 | 0 | 100 | 0 |
| | Johnsongrass | 2 | 95 | 9 | 0 | 100 | 0 | 0 | 100 | 0 | 0 | 100 | 0 |
| | Cocklebur | 3 | 30 | 9 | 2 | 20 | 9 | 2 | 70 | 9 | 1 | 80 | 9 |
| | Morningglory | 4 | 20 | 9 | 3 | 20 | 9 | 3 | 95 | 9 | 1 | 95 | 9 |
| | Purple Nutsedge | 3 | 0 | 9 | 2 | 0 | 9 | 0 | 100 | 0 | 0 | 100 | 0 |
| 2 | Lima Bean | 5 | 0 | 0 | 5 | 0 | 0 | 4 | 0 | 9 | 4 | 0 | 9 |
| | Wild Oat | 5 | 0 | 0 | 4 | 0 | 9 | 4 | 0 | 9 | 4 | 0 | 9 |
| | Barnyardgrass | 4 | 0 | 2 | 4 | 0 | 2 | 4 | 30 | 2 | 3 | 90 | 2 |
| | Green Foxtail | 5 | 0 | 0 | 5 | 0 | 0 | 5 | 0 | 0 | 5 | 0 | 0 |
| | Velvetleaf | 4 | 0 | 9 | 4 | 0 | 9 | 4 | 0 | 9 | 3 | 0 | 9 |
| | Tomato | 5 | 0 | 0 | 5 | 0 | 0 | 4 | 0 | 9 | 4 | 0 | 9 |
| | Field Bindweed | 5 | 0 | 0 | 5 | 0 | 0 | 4 | 0 | 9 | 4 | 0 | 9 |
| | Soybean | 5 | 0 | 0 | 5 | 0 | 0 | 5 | 0 | 0 | 4 | 0 | 9 |
| | Sorghum | 5 | 0 | 0 | 5 | 0 | 0 | 5 | 0 | 0 | 5 | 0 | 0 |
| | Wild Mustard | 4 | 0 | 9 | 4 | 0 | 9 | 4 | 0 | 9 | 4 | 0 | 9 |
| | Johnsongrass | 5 | 0 | 0 | 5 | 0 | 0 | 5 | 0 | 0 | 4 | 0 | 2 |
| | Cocklebur | 5 | 0 | 0 | 5 | 0 | 0 | 5 | 0 | 0 | 4 | 0 | 9 |
| | Morningglory | 4 | 0 | 9 | 4 | 0 | 9 | 4 | 0 | 2 | 4 | 0 | 9 |
| | Purple Nutsedge | | | | | | | | | | 5 | 0 | 0 |
| 3 | Lima Bean | 5 | 0 | 0 | 5 | 0 | 0 | 5 | 0 | 0 | 5 | 0 | 0 |
| | Wild Oat | 5 | 0 | 0 | 5 | 0 | 0 | 5 | 0 | 0 | 5 | 0 | 0 |
| | Barnyardgrass | 5 | 0 | 0 | 5 | 0 | 0 | 5 | 0 | 0 | 4 | 0 | 9 |
| | Green Foxtail | 5 | 0 | 0 | 5 | 0 | 0 | 4 | 0 | 9 | 4 | 0 | 9 |
| | Velvetleaf | 4 | 0 | 9 | 4 | 0 | 9 | 4 | 0 | 9 | 4 | 0 | 9 |
| | Tomato | 5 | 0 | 0 | 5 | 0 | 0 | 5 | 0 | 0 | 5 | 0 | 0 |
| | Field Bindweed | 5 | 0 | 0 | 5 | 0 | 0 | 5 | 0 | 0 | 5 | 0 | 0 |
| | Soybean | 5 | 0 | 0 | 5 | 0 | 0 | 5 | 0 | 0 | 5 | 0 | 0 |
| | Sorghum | 5 | 0 | 0 | 5 | 0 | 0 | 5 | 0 | 0 | 5 | 0 | 0 |
| | Wild Mustard | 5 | 0 | 0 | 5 | 0 | 0 | 5 | 0 | 0 | 5 | 0 | 0 |
| | Johnsongrass | 5 | 0 | 0 | 5 | 0 | 0 | 4 | 0 | 9 | 4 | 0 | 9 |
| | Cocklebur | 5 | 0 | 0 | 5 | 0 | 0 | 5 | 0 | 0 | 5 | 0 | 0 |
| | Morningglory | 5 | 0 | 0 | 4 | 0 | 9 | 4 | 0 | 9 | 4 | 0 | 9 |
| | Purple Nutsedge | | | | | | | | | | 5 | 0 | 0 |
| 4 | Lima Bean | 4 | 0 | 2 | 0 | 100 | 11 | 3 | 60 | 9 | 3 | 60 | 9 |
| | Soybean | 5 | 0 | 0 | 4 | 0 | 9 | 3 | 0 | 9 | 2 | 20 | 9 |
| | Cocklebur | 3 | 0 | 9 | 2 | 20 | 9 | 2 | 80 | 9 | 0 | 100 | 0 |
| | Peanut | 4 | 80 | 2 | 4 | 60 | 9 | 2 | 50 | 9 | 2 | 60 | 9 |
| | Cotton | 4 | 30 | 9 | 3 | 40 | 9 | 0 | 100 | 0 | 0 | 100 | 0 |
| | Green Foxtail | 0 | 100 | 0 | 0 | 100 | 0 | 0 | 100 | 0 | 0 | 100 | 0 |
| | Field Bindweed | 4 | 0 | 9 | 4 | 0 | 9 | 3 | 95 | 9 | 2 | 70 | 9 |
| | Tomato | 3 | 0 | 9 | 3 | 40 | 9 | 2 | 90 | 9 | 2 | 95 | 9 |
| | Wild Mustard | 3 | 0 | 9 | 3 | 0 | 9 | 3 | 0 | 9 | 1 | 95 | 9 |
| | Morningglory | 3 | 80 | 9 | 1 | 90 | 9 | 0 | 100 | 0 | 0 | 100 | 0 |
| | Barnyardgrass | 0 | 100 | 0 | 0 | 100 | 0 | 0 | 100 | 0 | 0 | 100 | 0 |
| | Wild Oat | 2 | 90 | 9 | 2 | 95 | 9 | 0 | 100 | 0 | 0 | 100 | 0 |
| | Velvetleaf | 0 | 100 | 0 | 0 | 100 | 0 | 0 | 100 | 0 | 0 | 100 | 0 |
| | Wild Buckwheat | 2 | 90 | 9 | 0 | 100 | 0 | 0 | 100 | 0 | 0 | 100 | 0 |
| | Johnsongrass | 1 | 95 | 9 | 1 | 90 | 9 | 1 | 95 | 9 | 1 | 95 | 9 |
| 5 | Lima Bean | 5 | 0 | 0 | 5 | 0 | 0 | 5 | 0 | 0 | 5 | 0 | 0 |
| | Soybean | 5 | 0 | 0 | 5 | 0 | 0 | 5 | 0 | 0 | 5 | 0 | 0 |
| | Cocklebur | 5 | 0 | 0 | 4 | 0 | 9 | 3 | 0 | 9 | 3 | 0 | 9 |
| | Peanut | 3 | 80 | 11 | 4 | 80 | 11 | 4 | 30 | 2 | 5 | 0 | 0 |
| | Cotton | 5 | 0 | 0 | 5 | 0 | 0 | 4 | 20 | 0 | 5 | 0 | 0 |
| | Green Foxtail | 4 | 0 | 9 | 4 | 0 | 9 | 4 | 0 | 9 | 4 | 0 | 9 |
| | Field Bindweed | 4 | 0 | 9 | 4 | 0 | 9 | 4 | 0 | 9 | 4 | 0 | 9 |
| | Tomato | 3 | 95 | 12 | 5 | 0 | 0 | 5 | 0 | 0 | 4 | 0 | 9 |
| | Wild Mustard | 5 | 0 | 0 | 5 | 0 | 0 | 5 | 0 | 0 | 5 | 0 | 0 |
| | Morningglory | 4 | 20 | 9 | 3 | 0 | 9 | 3 | 0 | 9 | 1 | 95 | 9 |
| | Barnyardgrass | 4 | 10 | 9 | 4 | 0 | 9 | 4 | 0 | 9 | 4 | 0 | 9 |
| | Wild Oat | 4 | 0 | 9 | 5 | 0 | 0 | 5 | 0 | 0 | 5 | 0 | 0 |
| | Velvetleaf | 3 | 0 | 9 | 3 | 0 | 9 | 3 | 0 | 9 | 3 | 50 | 9 |

TABLE 1-continued

Preemergence Herbicidal Activity of Certain Hydroxamic Acid Derivatives

| Cpd. of Ex. | Plant Species | Rate of Application - kg/ha | | | | | | | | | | |
|---|---|---|---|---|---|---|---|---|---|---|---|---|
| | | 0.500 | | | 1.000 | | | 2.000 | | | 4.000 | | |
| | | V | K | F | V | K | F | V | K | F | V | K | F |
| | Wild Buckwheat | 3 | 0 | 9 | 3 | 0 | 9 | 2 | 0 | 9 | 2 | 0 | 9 |
| | Johnsongrass | 4 | 0 | 9 | 4 | 0 | 9 | 4 | 0 | 9 | 4 | 0 | 9 |
| 6 | Lima Bean | 5 | 0 | 0 | 5 | 0 | 0 | 5 | 0 | 0 | 5 | 0 | 0 |
| | Soybean | 5 | 0 | 0 | 5 | 0 | 0 | 5 | 0 | 0 | 5 | 0 | 0 |
| | Cocklebur | 4 | 0 | 9 | 5 | 0 | 0 | 4 | 0 | 9 | 4 | 0 | 9 |
| | Peanut | 5 | 0 | 0 | 5 | 0 | 0 | 4 | 40 | 11 | 4 | 80 | 11 |
| | Cotton | 5 | 0 | 0 | 5 | 0 | 0 | 5 | 0 | 0 | 4 | 0 | 1 |
| | Green Foxtail | 5 | 0 | 0 | 5 | 0 | 0 | 5 | 0 | 0 | 5 | 0 | 0 |
| | Field Bindweed | 4 | 0 | 9 | 4 | 0 | 9 | 4 | 0 | 9 | 4 | 0 | 9 |
| | Tomato | 4 | 0 | 9 | 4 | 0 | 9 | 4 | 0 | 9 | 5 | 0 | 0 |
| | Wild Mustard | 5 | 0 | 0 | 5 | 0 | 0 | 5 | 0 | 0 | 5 | 0 | 0 |
| | Morningglory | 4 | 0 | 9 | 4 | 0 | 9 | 4 | 0 | 9 | 4 | 0 | 9 |
| | Barnyardgrass | 5 | 0 | 0 | 5 | 0 | 0 | 5 | 0 | 0 | 5 | 0 | 0 |
| | Wild Oat | 4 | 0 | 9 | 4 | 0 | 9 | 4 | 0 | 9 | 4 | 0 | 9 |
| | Velvetleaf | 3 | 0 | 9 | 3 | 0 | 9 | 3 | 0 | 9 | 3 | 0 | 9 |
| | Wild Buckwheat | 4 | 0 | 9 | 4 | 0 | 9 | 4 | 0 | 9 | 4 | 0 | 9 |
| | Johnsongrass | 5 | 0 | 0 | 5 | 0 | 0 | 5 | 0 | 0 | 5 | 0 | 0 |
| 7 | Lima Bean | 4 | 0 | 2 | 4 | 0 | 9 | 4 | 0 | 9 | 4 | 0 | 9 |
| | Soybean | 5 | 0 | 0 | 5 | 0 | 0 | 4 | 0 | 9 | 5 | 0 | 0 |
| | Cocklebur | 4 | 0 | 9 | 4 | 0 | 9 | 3 | 0 | 9 | 2 | 20 | 9 |
| | Peanut | 5 | 0 | 0 | 5 | 0 | 0 | 5 | 0 | 0 | 4 | 0 | 9 |
| | Cotton | 5 | 0 | 0 | 5 | 0 | 0 | 5 | 0 | 0 | 4 | 0 | 9 |
| | Green Foxtail | 5 | 0 | 0 | 4 | 0 | 9 | 4 | 0 | 9 | 3 | 0 | 9 |
| | Field Bindweed | 4 | 0 | 9 | 4 | 0 | 9 | 4 | 0 | 9 | 4 | 0 | 9 |
| | Tomato | 4 | 0 | 9 | 4 | 0 | 9 | 4 | 0 | 9 | 4 | 0 | 9 |
| | Wild Mustard | 4 | 0 | 9 | 5 | 0 | 0 | 4 | 0 | 9 | 5 | 0 | 0 |
| | Morningglory | 4 | 0 | 9 | 5 | 0 | 0 | 5 | 0 | 0 | 4 | 0 | 9 |
| | Barnyardgrass | 4 | 0 | 9 | 4 | 0 | 9 | 4 | 0 | 9 | 4 | 40 | 9 |
| | Wild Oat | 4 | 0 | 9 | 4 | 0 | 9 | 4 | 0 | 9 | 4 | 0 | 9 |
| | Velvetleaf | 3 | 0 | 9 | 3 | 0 | 9 | 3 | 0 | 9 | 3 | 0 | 9 |
| | Wild Buckwheat | 3 | 0 | 9 | 2 | 0 | 9 | 2 | 0 | 9 | 2 | 0 | 9 |
| | Johnsongrass | 4 | 0 | 9 | 4 | 0 | 9 | 4 | 0 | 9 | 4 | 0 | 9 |
| 8 | Lima Bean | 5 | 0 | 0 | 5 | 0 | 0 | 4 | 0 | 9 | 4 | 0 | 9 |
| | Soybean | 5 | 0 | 0 | 5 | 0 | 0 | 5 | 0 | 0 | 4 | 0 | 9 |
| | Cocklebur | 4 | 0 | 9 | 3 | 0 | 9 | 2 | 70 | 9 | 2 | 10 | 9 |
| | Purple Nutsedge | 5 | 0 | 0 | 4 | 0 | 9 | 3 | 0 | 9 | 2 | 20 | 9 |
| | Peanut | 5 | 0 | 0 | 5 | 0 | 0 | 4 | 0 | 0 | 4 | 0 | 0 |
| | Cotton | 5 | 0 | 0 | 4 | 0 | 9 | 4 | 10 | 9 | 2 | 95 | 9 |
| | Green Foxtail | 3 | 75 | 9 | 0 | 100 | 0 | 0 | 100 | 0 | 0 | 100 | 0 |
| | Field Bindweed | 3 | 0 | 9 | 2 | 80 | 9 | 2 | 85 | 9 | 0 | 100 | 0 |
| | Tomato | 0 | 100 | 0 | 0 | 100 | 0 | 0 | 100 | 0 | 0 | 100 | 0 |
| | Wild Mustard | 4 | 0 | 9 | 3 | 20 | 9 | 2 | 75 | 9 | 0 | 100 | 0 |
| | Morningglory | 3 | 0 | 9 | 4 | 80 | 9 | 2 | 90 | 9 | 2 | 95 | 9 |
| | Wild Oat | 3 | 65 | 9 | 3 | 85 | 9 | 2 | 95 | 9 | 0 | 100 | 0 |
| | Barnyardgrass | 0 | 100 | 0 | 0 | 100 | 0 | 0 | 100 | 0 | 0 | 100 | 0 |
| | Velvetleaf | 3 | 70 | 9 | 0 | 100 | 0 | 0 | 100 | 0 | 0 | 100 | 0 |
| | Wild Buckwheat | 3 | 10 | 9 | 3 | 0 | 9 | 2 | 40 | 9 | 2 | 40 | 9 |
| | Johnsongrass | 0 | 100 | 0 | 0 | 100 | 0 | 0 | 100 | 0 | 0 | 100 | 0 |
| 9 | Lima Bean | 5 | 0 | 0 | 5 | 0 | 0 | 5 | 0 | 0 | 5 | 0 | 0 |
| | Soybean | 5 | 0 | 0 | 5 | 0 | 0 | 5 | 0 | 0 | 5 | 0 | 0 |
| | Cocklebur | 5 | 0 | 0 | 5 | 0 | 0 | 5 | 0 | 0 | 5 | 0 | 0 |
| | Peanut | 5 | 0 | 0 | 5 | 0 | 0 | 5 | 0 | 0 | 5 | 0 | 0 |
| | Cotton | 5 | 0 | 0 | 5 | 0 | 0 | 5 | 0 | 0 | 5 | 0 | 0 |
| | Green Foxtail | 5 | 0 | 0 | 5 | 0 | 0 | 5 | 0 | 0 | 4 | 0 | 9 |
| | Field Bindweed | 5 | 0 | 0 | 5 | 0 | 0 | 5 | 0 | 0 | 4 | 0 | 9 |
| | Tomato | 5 | 0 | 0 | 5 | 0 | 0 | 5 | 0 | 0 | 4 | 0 | 9 |
| | Wild Mustard | 5 | 0 | 0 | 5 | 0 | 0 | 5 | 0 | 0 | 5 | 0 | 0 |
| | Morningglory | 4 | 0 | 9 | 4 | 0 | 9 | 3 | 0 | 9 | 3 | 20 | 9 |
| | Barnyardgrass | 5 | 0 | 0 | 5 | 0 | 0 | 4 | 0 | 9 | 4 | 10 | 9 |
| | Wild Oat | 5 | 0 | 0 | 5 | 0 | 0 | 5 | 0 | 0 | 4 | 0 | 9 |
| | Velvetleaf | 5 | 0 | 0 | 4 | 0 | 9 | 4 | 0 | 9 | 3 | 30 | 9 |
| | Wild Buckwheat | 5 | 0 | 0 | 4 | 0 | 2 | 4 | 0 | 9 | 3 | 0 | 9 |
| | Johnsongrass | 5 | 0 | 0 | 4 | 10 | 9 | 4 | 20 | 9 | 2 | 90 | 9 |
| 10 | Lima Bean | 5 | 0 | 0 | 4 | 0 | 9 | 4 | 0 | 9 | 3 | 60 | 9 |
| | Wild Oat | 4 | 90 | 9 | 4 | 90 | 9 | 0 | 100 | 0 | 2 | 95 | 9 |
| | Barnyardgrass | 3 | 95 | 9 | 0 | 100 | 0 | 0 | 100 | 0 | 0 | 100 | 0 |
| | Green Foxtail | 4 | 0 | 9 | 4 | 80 | 2 | 3 | 70 | 9 | 3 | 95 | 9 |
| | Velvetleaf | 3 | 95 | 9 | 3 | 70 | 9 | 2 | 80 | 9 | 2 | 90 | 9 |
| | Tomato | 4 | 0 | 9 | 4 | 30 | 9 | 3 | 0 | 9 | 2 | 50 | 9 |
| | Field Bindweed | 4 | 50 | 9 | 3 | 80 | 9 | 3 | 90 | 2 | 0 | 100 | 0 |
| | Wild Mustard | 0 | 100 | 0 | 0 | 100 | 0 | 0 | 100 | 0 | 0 | 100 | 0 |
| | Morningglory | 3 | 0 | 9 | 3 | 60 | 2 | 3 | 30 | 9 | 3 | 80 | 9 |
| | Soybean | 0 | 100 | 11 | 5 | 0 | 0 | 5 | 0 | 0 | 0 | 100 | 11 |
| | Cocklebur | 4 | 0 | 9 | 3 | 0 | 9 | 3 | 20 | 9 | 3 | 80 | 9 |
| | Wild Buckwheat | 4 | 0 | 9 | 4 | 70 | 9 | 2 | 95 | 9 | 2 | 70 | 9 |
| | Johnsongrass | 3 | 20 | 9 | 4 | 10 | 9 | 1 | 95 | 9 | 3 | 90 | 9 |

TABLE 1-continued

Preemergence Herbicidal Activity of Certain Hydroxamic Acid Derivatives

| Cpd. of Ex. | Plant Species | 0.500 | | | 1.000 | | | 2.000 | | | 4.000 | | |
|---|---|---|---|---|---|---|---|---|---|---|---|---|---|
| | | V | K | F | V | K | F | V | K | F | V | K | F |
| | Purple Nutsedge | | | | | | | | | | 4 | 0 | 9 |
| 11 | Lima Bean | 4 | 0 | 9 | 2 | 0 | 9 | 2 | 0 | 9 | 2 | 0 | 9 |
| | Wild Oat | 4 | 0 | 9 | 3 | 30 | 9 | 2 | 95 | 9 | 0 | 100 | 0 |
| | Barnyardgrass | 3 | 80 | 9 | 2 | 95 | 9 | 0 | 100 | 0 | 0 | 100 | 0 |
| | Green Foxtail | 4 | 0 | 9 | 4 | 0 | 9 | 3 | 50 | 9 | 3 | 80 | 9 |
| | Velvetleaf | 3 | 0 | 9 | 3 | 0 | 9 | 2 | 70 | 9 | 2 | 80 | 9 |
| | Tomato | 5 | 0 | 0 | 4 | 0 | 9 | 4 | 0 | 9 | 3 | 80 | 9 |
| | Field Bindweed | 4 | 0 | 9 | 4 | 0 | 9 | 3 | 0 | 9 | 3 | 0 | 9 |
| | Wild Mustard | 5 | 0 | 0 | 3 | 0 | 9 | 3 | 0 | 2 | 2 | 0 | 9 |
| | Morningglory | 2 | 0 | 9 | 2 | 0 | 9 | 2 | 0 | 9 | 2 | 60 | 9 |
| | Soybean | 5 | 0 | 0 | 0 | 100 | 11 | 0 | 100 | 11 | 0 | 100 | 11 |
| | Cocklebur | 3 | 0 | 9 | 2 | 0 | 9 | 2 | 20 | 9 | 2 | 60 | 9 |
| | Wild Buckwheat | 2 | 0 | 9 | 2 | 0 | 9 | 2 | 30 | 9 | 2 | 80 | 9 |
| | Johnsongrass | 3 | 20 | 9 | 2 | 90 | 9 | 1 | 70 | 9 | 1 | 20 | 9 |
| | Purple Nutsedge | | | | | | | | | | 2 | 20 | 9 |
| 12 | Lima Bean | 3 | 0 | 9 | 3 | 0 | 9 | | | | 3 | 40 | 9 |
| | Wild Oat | 2 | 90 | 9 | 0 | 100 | 0 | | | | 0 | 100 | 0 |
| | Barnyardgrass | 0 | 100 | 0 | 0 | 100 | 0 | | | | 0 | 100 | 0 |
| | Green Foxtail | 2 | 95 | 9 | 2 | 95 | 9 | | | | 0 | 100 | 0 |
| | Velvetleaf | 1 | 95 | 9 | 0 | 100 | 0 | | | | 0 | 100 | 0 |
| | Soybean | 5 | 0 | 0 | 5 | 0 | 0 | | | | 3 | 0 | 9 |
| | Hemp Sesbania | 4 | 0 | 9 | 3 | 0 | 9 | | | | 3 | 70 | 9 |
| | Morningglory | 0 | 100 | 0 | 0 | 100 | 0 | | | | 0 | 100 | 0 |
| | Cocklebur | 3 | 0 | 9 | 3 | 80 | 9 | | | | 3 | 50 | 9 |
| | Field Bindweed | 3 | 0 | 9 | 3 | 0 | 9 | | | | 2 | 95 | 9 |
| | Tomato | 3 | 60 | 9 | 3 | 60 | 9 | | | | 2 | 90 | 9 |
| | Wild Mustard | 0 | 100 | 0 | 2 | 95 | 9 | | | | 0 | 100 | 0 |
| | Johnsongrass | 1 | 95 | 9 | 0 | 100 | 0 | | | | 0 | 100 | 0 |
| | Yellow Nutsedge | 4 | 0 | 9 | 4 | 0 | 9 | | | | 3 | 20 | 9 |
| 13 | Lima Bean | 4 | 0 | 9 | 3 | 0 | 9 | 3 | 0 | 9 | 2 | 80 | 9 |
| | Wild Oat | 3 | 70 | 9 | 2 | 95 | 9 | 1 | 95 | 9 | 0 | 100 | 0 |
| | Barnyardgrass | 0 | 100 | 0 | 0 | 100 | 0 | 0 | 100 | 0 | 0 | 100 | 0 |
| | Green Foxtail | 3 | 95 | 9 | 0 | 100 | 0 | 0 | 100 | 0 | 0 | 100 | 0 |
| | Velvetleaf | 2 | 95 | 9 | 1 | 95 | 9 | 1 | 95 | 9 | 0 | 100 | 0 |
| | Soybean | 5 | 0 | 0 | 5 | 0 | 0 | 3 | 0 | 9 | 3 | 0 | 9 |
| | Hemp Sesbania | 5 | 0 | 0 | 4 | 0 | 9 | 3 | 10 | 9 | 3 | 70 | 9 |
| | Morningglory | 2 | 80 | 9 | 0 | 100 | 0 | 0 | 100 | 0 | 0 | 100 | 0 |
| | Cocklebur | 3 | 20 | 9 | 3 | 80 | 9 | 0 | 100 | 0 | 0 | 100 | 0 |
| | Field Bindweed | 3 | 0 | 9 | 3 | 95 | 2 | 2 | 90 | 9 | 0 | 100 | 0 |
| | Tomato | 3 | 0 | 9 | 3 | 80 | 9 | 2 | 30 | 9 | 2 | 90 | 9 |
| | Wild Mustard | 3 | 60 | 9 | 2 | 60 | 9 | 0 | 100 | 0 | 0 | 100 | 0 |
| | Johnsongrass | 0 | 100 | 0 | 0 | 100 | 0 | 1 | 80 | 9 | 1 | 90 | 9 |
| | Yellow Nutsedge | 5 | 0 | 0 | 4 | 0 | 9 | 3 | 0 | 9 | 2 | 0 | 9 |
| 14 | Lima Bean | 4 | 0 | 9 | 4 | 0 | 9 | 3 | 20 | 9 | 2 | 60 | 9 |
| | Wild Oat | 3 | 30 | 9 | 3 | 90 | 0 | 0 | 100 | 0 | 0 | 100 | 0 |
| | Barnyardgrass | 0 | 100 | 0 | 0 | 100 | 0 | 0 | 100 | 0 | 0 | 100 | 0 |
| | Green Foxtail | 4 | 0 | 9 | 3 | 10 | 9 | 0 | 100 | 0 | 0 | 100 | 0 |
| | Velvetleaf | 3 | 10 | 9 | 2 | 10 | 9 | 0 | 100 | 0 | 0 | 100 | 0 |
| | Soybean | 5 | 0 | 0 | 5 | 0 | 0 | 5 | 0 | 0 | 4 | 0 | 9 |
| | Hemp Sesbania | 5 | 0 | 0 | 4 | 0 | 2 | 3 | 0 | 9 | 3 | 0 | 9 |
| | Morningglory | 3 | 0 | 9 | 3 | 0 | 9 | 2 | 90 | 9 | 1 | 90 | 9 |
| | Cocklebur | 3 | 0 | 9 | 3 | 0 | 9 | 3 | 40 | 9 | 0 | 100 | 0 |
| | Field Bindweed | 4 | 0 | 9 | 4 | 0 | 9 | 3 | 20 | 9 | 2 | 95 | 9 |
| | Tomato | 3 | 0 | 9 | 3 | 0 | 9 | 3 | 0 | 9 | 2 | 60 | 9 |
| | Wild Mustard | 4 | 0 | 9 | 3 | 0 | 9 | 3 | 30 | 9 | 0 | 100 | 0 |
| | Johnsongrass | 3 | 80 | 9 | 0 | 100 | 0 | 0 | 100 | 0 | 1 | 95 | 9 |
| | Yellow Nutsedge | 5 | 0 | 0 | 5 | 0 | 0 | 4 | 0 | 9 | 3 | 40 | 9 |
| 16 | Lima Bean | 4 | 0 | 2 | 3 | 40 | 9 | 2 | 0 | 9 | 1 | 60 | 9 |
| | Wild Oat | 0 | 100 | 0 | 0 | 100 | 0 | 0 | 100 | 0 | 0 | 100 | 0 |
| | Barnyardgrass | 0 | 100 | 0 | 0 | 100 | 0 | 0 | 100 | 0 | 0 | 100 | 0 |
| | Green Foxtail | 0 | 100 | 0 | 0 | 100 | 0 | 0 | 100 | 0 | 0 | 100 | 0 |
| | Velvetleaf | 0 | 100 | 0 | 0 | 100 | 0 | 0 | 100 | 0 | 0 | 100 | 0 |
| | Tomato | 2 | 0 | 9 | 1 | 30 | 9 | 0 | 100 | 0 | 0 | 100 | 0 |
| | Field Bindweed | 3 | 30 | 9 | 3 | 90 | 2 | 0 | 100 | 0 | 0 | 100 | 0 |
| | Soybean | 5 | 0 | 0 | 4 | 0 | 2 | 4 | 0 | 9 | 3 | 0 | 9 |
| | Sorghum | 0 | 100 | 0 | 0 | 100 | 0 | 0 | 100 | 0 | 0 | 100 | 0 |
| | Wild Mustard | 2 | 50 | 9 | 2 | 95 | 9 | 0 | 100 | 0 | 0 | 100 | 0 |
| | Johnsongrass | 0 | 100 | 0 | 0 | 100 | 0 | 0 | 100 | 0 | 0 | 100 | 0 |
| | Cocklebur | 2 | 20 | 9 | 2 | 60 | 9 | 0 | 100 | 0 | 0 | 100 | 0 |
| | Morningglory | 4 | 20 | 9 | 4 | 80 | 9 | 1 | 90 | 9 | 0 | 100 | 0 |
| | Purple Nutsedge | 4 | 10 | 9 | 2 | 0 | 9 | 0 | 100 | 0 | 1 | 0 | 9 |
| 17 | Lima Bean | 5 | 0 | 0 | 5 | 0 | 0 | 5 | 0 | 0 | 4 | 0 | 2 |
| | Wild Oat | 5 | 0 | 0 | 5 | 0 | 0 | 5 | 0 | 0 | 4 | 60 | 1 |
| | Barnyardgrass | 5 | 0 | 0 | 5 | 0 | 0 | 5 | 0 | 0 | 4 | 0 | 2 |
| | Green Foxtail | 5 | 0 | 0 | 5 | 0 | 0 | 5 | 0 | 0 | 3 | 95 | 9 |
| | Velvetleaf | 4 | 0 | 9 | 4 | 0 | 9 | 4 | 0 | 9 | 4 | 0 | 9 |

TABLE 1-continued

Preemergence Herbicidal Activity of Certain Hydroxamic Acid Derivatives

| Cpd. of Ex. | Plant Species | Rate of Application - kg/ha | | | | | | | | | | |
|---|---|---|---|---|---|---|---|---|---|---|---|---|
| | | 0.500 | | | 1.000 | | | 2.000 | | | 4.000 | | |
| | | V | K | F | V | K | F | V | K | F | V | K | F |
| | Tomato | 5 | 0 | 0 | 5 | 0 | 0 | 5 | 0 | 0 | 5 | 0 | 0 |
| | Field Bindweed | 4 | 0 | 9 | 5 | 0 | 0 | 5 | 0 | 0 | 4 | 0 | 2 |
| | Soybean | 5 | 0 | 0 | 5 | 0 | 0 | 5 | 0 | 0 | 5 | 0 | 0 |
| | Sorghum | 5 | 0 | 0 | 5 | 0 | 0 | 5 | 0 | 0 | 5 | 0 | 0 |
| | Wild Mustard | 5 | 0 | 0 | 5 | 0 | 0 | 5 | 0 | 0 | 5 | 0 | 0 |
| | Johnsongrass | 5 | 0 | 0 | 5 | 0 | 0 | 5 | 0 | 0 | 4 | 0 | 9 |
| | Cocklebur | 5 | 0 | 0 | 5 | 0 | 0 | 5 | 0 | 0 | 5 | 0 | 0 |
| | Morningglory | 5 | 0 | 0 | 5 | 0 | 0 | 4 | 0 | 9 | 4 | 0 | 9 |
| | Purple Nutsedge | | | | | | | | | | 0 | 100 | 11 |
| 18 | Lima Bean | 4 | 0 | 0 | 3 | 0 | 9 | 2 | 0 | 9 | 2 | 60 | 9 |
| | Soybean | 4 | 0 | 9 | 4 | 0 | 9 | 2 | 0 | 9 | 2 | 20 | 9 |
| | Cocklebur | 3 | 0 | 9 | 3 | 20 | 9 | 2 | 90 | 9 | 0 | 100 | 0 |
| | Peanut | 3 | 50 | 2 | 3 | 0 | 9 | 2 | 0 | 9 | 3 | 80 | 9 |
| | Cotton | 4 | 20 | 9 | 2 | 70 | 9 | 0 | 100 | 0 | 0 | 100 | 0 |
| | Green Foxtail | 3 | 90 | 9 | 2 | 90 | 9 | 0 | 100 | 0 | 1 | 95 | 9 |
| | Field Bindweed | 4 | 0 | 9 | 4 | 20 | 9 | 3 | 40 | 9 | 2 | 80 | 9 |
| | Tomato | 3 | 0 | 9 | 2 | 0 | 9 | 2 | 70 | 9 | 1 | 90 | 9 |
| | Wild Mustard | 3 | 0 | 9 | 3 | 0 | 9 | 3 | 0 | 9 | 2 | 50 | 9 |
| | Morningglory | 0 | 100 | 0 | 0 | 100 | 0 | 0 | 100 | 0 | 0 | 100 | 0 |
| | Barnyardgrass | 0 | 100 | 0 | 0 | 100 | 0 | 0 | 100 | 0 | 0 | 100 | 0 |
| | Wild Oat | 3 | 40 | 9 | 0 | 100 | 0 | 0 | 100 | 0 | 0 | 100 | 0 |
| | Velvetleaf | 0 | 100 | 0 | 0 | 100 | 0 | 0 | 100 | 0 | 0 | 100 | 0 |
| | Wild Buckwheat | 0 | 100 | 0 | 0 | 100 | 0 | 0 | 100 | 0 | 0 | 100 | 0 |
| | Johnsongrass | 1 | 95 | 9 | 1 | 95 | 9 | 1 | 95 | 9 | 1 | 60 | 9 |
| 19 | Lima Bean | 5 | 0 | 0 | 5 | 0 | 0 | 5 | 0 | 0 | 5 | 0 | 0 |
| | Soybean | 5 | 0 | 0 | 5 | 0 | 0 | 5 | 0 | 0 | 5 | 0 | 0 |
| | Cocklebur | 4 | 0 | 9 | 4 | 0 | 9 | 3 | 0 | 9 | 3 | 20 | 9 |
| | Peanut | 4 | 80 | 11 | 4 | 0 | 2 | 4 | 0 | 2 | 4 | 50 | 2 |
| | Cotton | 5 | 0 | 0 | 5 | 0 | 0 | 5 | 0 | 0 | 4 | 0 | 1 |
| | Green Foxtail | 4 | 0 | 9 | 5 | 0 | 0 | 4 | 0 | 9 | 4 | 0 | 9 |
| | Field Bindweed | 4 | 0 | 9 | 4 | 0 | 2 | 4 | 0 | 9 | 4 | 0 | 9 |
| | Tomato | 4 | 0 | 9 | 5 | 0 | 0 | 4 | 0 | 9 | 3 | 95 | 2 |
| | Wild Mustard | 5 | 0 | 0 | 5 | 0 | 0 | 5 | 0 | 0 | 5 | 0 | 0 |
| | Morningglory | 3 | 0 | 9 | 3 | 60 | 9 | 3 | 70 | 9 | 0 | 100 | 0 |
| | Barnyardgrass | 5 | 0 | 0 | 4 | 0 | 9 | 4 | 0 | 9 | 3 | 0 | 9 |
| | Wild Oat | 4 | 0 | 9 | 4 | 0 | 9 | 5 | 0 | 0 | 4 | 0 | 1 |
| | Velvetleaf | 3 | 0 | 9 | 3 | 0 | 9 | 3 | 0 | 9 | 2 | 0 | 9 |
| | Wild Buckwheat | 3 | 0 | 9 | 3 | 0 | 9 | 2 | 0 | 9 | 2 | 0 | 9 |
| | Johnsongrass | 4 | 0 | 9 | 4 | 0 | 9 | 4 | 0 | 9 | 4 | 0 | 9 |
| 20 | Lima Bean | 5 | 0 | 0 | 5 | 0 | 0 | 5 | 0 | 0 | 5 | 0 | 0 |
| | Soybean | 5 | 0 | 0 | 5 | 0 | 0 | 5 | 0 | 0 | 5 | 0 | 0 |
| | Cocklebur | 4 | 0 | 9 | 4 | 0 | 9 | 4 | 0 | 9 | 4 | 0 | 9 |
| | Peanut | 5 | 0 | 0 | 3 | 80 | 11 | 5 | 0 | 0 | 5 | 0 | 0 |
| | Cotton | 5 | 0 | 0 | 5 | 0 | 0 | 4 | 60 | 11 | 5 | 0 | 0 |
| | Green Foxtail | 5 | 0 | 0 | 5 | 0 | 0 | 5 | 0 | 0 | 5 | 0 | 0 |
| | Field Bindweed | 4 | 0 | 9 | 4 | 0 | 9 | 5 | 0 | 0 | 4 | 0 | 9 |
| | Tomato | 4 | 0 | 9 | 4 | 0 | 9 | 5 | 0 | 0 | 4 | 0 | 9 |
| | Wild Mustard | 5 | 0 | 0 | 4 | 0 | 9 | 5 | 0 | 0 | 5 | 0 | 0 |
| | Morningglory | 5 | 0 | 0 | 4 | 0 | 9 | 5 | 0 | 0 | 4 | 0 | 9 |
| | Barnyardgrass | 5 | 0 | 0 | 5 | 0 | 0 | 5 | 0 | 0 | 5 | 0 | 0 |
| | Wild Oat | 4 | 0 | 9 | 4 | 0 | 9 | 4 | 0 | 9 | 4 | 0 | 9 |
| | Velvetleaf | 3 | 0 | 9 | 3 | 0 | 9 | 3 | 0 | 9 | 3 | 0 | 9 |
| | Wild Buckwheat | 4 | 0 | 9 | 4 | 0 | 9 | 4 | 0 | 9 | 4 | 0 | 9 |
| | Johnsongrass | 4 | 0 | 9 | 4 | 0 | 9 | 5 | 0 | 0 | 4 | 0 | 9 |
| 21 | Lima Bean | 5 | 0 | 0 | 4 | 0 | 9 | 4 | 0 | 2 | 4 | 0 | 9 |
| | Soybean | 5 | 0 | 0 | 5 | 0 | 0 | 5 | 0 | 0 | 5 | 0 | 0 |
| | Cocklebur | 3 | 0 | 9 | 3 | 0 | 9 | 2 | 0 | 9 | 2 | 0 | 9 |
| | Peanut | 5 | 0 | 0 | 5 | 0 | 0 | 3 | 80 | 11 | 4 | 0 | 9 |
| | Cotton | 5 | 0 | 0 | 4 | 0 | 9 | 4 | 0 | 0 | 4 | 0 | 9 |
| | Green Foxtail | 4 | 0 | 9 | 4 | 0 | 9 | 4 | 20 | 9 | 4 | 0 | 9 |
| | Field Bindweed | 3 | 0 | 9 | 3 | 0 | 9 | 3 | 0 | 9 | 3 | 0 | 9 |
| | Tomato | 3 | 0 | 9 | 3 | 0 | 9 | 3 | 0 | 9 | 3 | 0 | 9 |
| | Wild Mustard | 4 | 0 | 9 | 4 | 0 | 9 | 3 | 0 | 9 | 3 | 0 | 9 |
| | Morningglory | 4 | 0 | 9 | 4 | 0 | 9 | 3 | 30 | 2 | 3 | 50 | 9 |
| | Barnyardgrass | 4 | 0 | 9 | 3 | 0 | 9 | 3 | 20 | 9 | 2 | 30 | 9 |
| | Wild Oat | 3 | 0 | 9 | 2 | 0 | 9 | 2 | 0 | 9 | 2 | 10 | 9 |
| | Velvetleaf | 2 | 0 | 9 | 2 | 0 | 9 | 2 | 0 | 9 | 2 | 0 | 9 |
| | Wild Buckwheat | 2 | 0 | 9 | 2 | 0 | 9 | 2 | 0 | 9 | 2 | 0 | 9 |
| | Johnsongrass | 3 | 0 | 9 | 3 | 40 | 9 | 2 | 10 | 9 | 2 | 20 | 9 |
| 22 | Lima Bean | 5 | 0 | 0 | 4 | 0 | 0 | 4 | 0 | 9 | 4 | 0 | 0 |
| | Soybean | 5 | 0 | 0 | 4 | 0 | 0 | 5 | 0 | 0 | 4 | 0 | 9 |
| | Cocklebur | 4 | 0 | 9 | 3 | 60 | 9 | 2 | 0 | 9 | 2 | 0 | 9 |
| | Purple Nutsedge | 4 | 0 | 9 | 3 | 0 | 9 | 2 | 0 | 9 | 2 | 0 | 9 |
| | Peanut | 5 | 0 | 0 | 4 | 0 | 0 | 5 | 0 | 0 | 4 | 0 | 9 |
| | Cotton | 5 | 0 | 0 | 4 | 0 | 9 | 4 | 0 | 9 | 2 | 90 | 9 |
| | Green Foxtail | 3 | 40 | 9 | 0 | 100 | 0 | 0 | 100 | 0 | 0 | 100 | 0 |

TABLE 1-continued
Preemergence Herbicidal Activity of Certain Hydroxamic Acid Derivatives

| Cpd. of Ex. | Plant Species | Rate of Application - kg/ha | | | | | | | | | | |
|---|---|---|---|---|---|---|---|---|---|---|---|---|
| | | 0.500 | | | 1.000 | | | 2.000 | | | 4.000 | | |
| | | V | K | F | V | K | F | V | K | F | V | K | F |
| | Field Bindweed | 3 | 10 | 9 | 3 | 20 | 9 | 2 | 95 | 9 | 0 | 100 | 0 |
| | Tomato | 2 | 70 | 9 | 0 | 100 | 0 | 0 | 100 | 0 | 0 | 100 | 0 |
| | Wild Mustard | 4 | 0 | 9 | 3 | 0 | 9 | 2 | 90 | 9 | 0 | 100 | 0 |
| | Morningglory | 4 | 0 | 9 | 3 | 20 | 9 | 0 | 100 | 0 | 0 | 100 | 0 |
| | Wild Oat | 4 | 0 | 9 | 0 | 100 | 0 | 0 | 100 | 0 | 0 | 100 | 0 |
| | Barnyardgrass | 0 | 100 | 0 | 0 | 100 | 0 | 0 | 100 | 0 | 0 | 100 | 0 |
| | Velvetleaf | 3 | 0 | 9 | 2 | 85 | 9 | 0 | 100 | 0 | 0 | 100 | 0 |
| | Wild Buckwheat | 3 | 0 | 9 | 3 | 0 | 9 | 2 | 85 | 9 | 2 | 95 | 9 |
| | Johnsongrass | 2 | 95 | 9 | 0 | 100 | 0 | 0 | 100 | 0 | 0 | 100 | 0 |
| 23(A) | Lima Bean | 4 | 60 | 11 | 4 | 0 | 0 | 4 | 0 | 0 | 0 | 100 | 11 |
| | Wild Oat | 4 | 70 | 9 | 3 | 90 | 9 | 3 | 95 | 9 | 0 | 100 | 0 |
| | Barnyardgrass | 3 | 90 | 9 | 0 | 100 | 0 | 0 | 100 | 0 | 0 | 100 | 0 |
| | Green Foxtail | 4 | 30 | 9 | 3 | 30 | 9 | 3 | 90 | 9 | 3 | 90 | 2 |
| | Velvetleaf | 3 | 60 | 9 | 3 | 90 | 9 | 3 | 90 | 2 | 2 | 90 | 1 |
| | Tomato | 4 | 0 | 9 | 3 | 0 | 9 | 2 | 80 | 9 | 2 | 30 | 9 |
| | Field Bindweed | 4 | 0 | 9 | 4 | 80 | 9 | 4 | 95 | 2 | 3 | 40 | 9 |
| | Wild Mustard | 0 | 100 | 0 | 0 | 100 | 0 | 0 | 100 | 0 | 0 | 100 | 0 |
| | Morningglory | 3 | 0 | 9 | 3 | 0 | 2 | 3 | 80 | 9 | 2 | 0 | 9 |
| | Soybean | 0 | 100 | 11 | 0 | 100 | 11 | 5 | 0 | 0 | 0 | 100 | 11 |
| | Cocklebur | 4 | 0 | 9 | 3 | 40 | 9 | 2 | 50 | 9 | 0 | 100 | 0 |
| | Wild Buckwheat | 4 | 0 | 9 | 4 | 0 | 9 | 4 | 20 | 9 | 2 | 90 | 9 |
| | Johnsongrass | 4 | 0 | 9 | 3 | 0 | 9 | 3 | 20 | 9 | 3 | 30 | 9 |
| | Purple Nutsedge | | | | | | | | | | 5 | 0 | 0 |
| 23(B) | Lima Bean | 2 | 0 | 9 | 2 | 0 | 9 | 1 | 0 | 9 | 1 | 20 | 9 |
| | Wild Oat | 2 | 95 | 9 | 0 | 100 | 0 | 1 | 95 | 9 | 0 | 100 | 0 |
| | Barnyardgrass | 0 | 100 | 0 | 0 | 100 | 0 | 0 | 100 | 0 | 0 | 100 | 0 |
| | Green Foxtail | 4 | 30 | 9 | 3 | 70 | 9 | 3 | 95 | 9 | 2 | 95 | 9 |
| | Velvetleaf | 0 | 100 | 0 | 1 | 95 | 0 | 1 | 90 | 9 | 1 | 95 | 9 |
| | Tomato | 2 | 50 | 9 | 2 | 90 | 9 | 1 | 95 | 9 | 1 | 90 | 9 |
| | Field Bindweed | 2 | 50 | 9 | 2 | 95 | 9 | 2 | 95 | 9 | 0 | 100 | 0 |
| | Wild Mustard | 2 | 80 | 9 | 2 | 90 | 9 | 2 | 90 | 9 | 0 | 100 | 0 |
| | Morningglory | 2 | 0 | 9 | 2 | 40 | 9 | 1 | 20 | 9 | 1 | 50 | 9 |
| | Soybean | 0 | 100 | 11 | 0 | 100 | 11 | 0 | 100 | 11 | 0 | 100 | 11 |
| | Cocklebur | 3 | 0 | 9 | 3 | 0 | 9 | 2 | 20 | 9 | 2 | 60 | 9 |
| | Wild Buckwheat | 3 | 0 | 9 | 3 | 0 | 9 | 2 | 0 | 9 | 2 | 30 | 9 |
| | Johnsongrass | 3 | 90 | 9 | 1 | 90 | 9 | 1 | 90 | 9 | 1 | 90 | 9 |
| | Purple Nutsedge | | | | | | | | | | 1 | 0 | 9 |
| | Lima Bean | 3 | 0 | 9 | 2 | 0 | 9 | 2 | 0 | 9 | 1 | 20 | 9 |
| | Wild Oat | 4 | 70 | 9 | 4 | 80 | 9 | 2 | 90 | 9 | 2 | 95 | 9 |
| | Barnyardgrass | 3 | 80 | 9 | 3 | 60 | 9 | 2 | 95 | 9 | 0 | 100 | 0 |
| | Green Foxtail | 4 | 0 | 9 | 4 | 10 | 9 | 3 | 20 | 9 | 3 | 80 | 9 |
| | Velvetleaf | 3 | 0 | 9 | 2 | 10 | 9 | 2 | 30 | 9 | 2 | 80 | 9 |
| | Tomato | 4 | 0 | 9 | 4 | 0 | 9 | 3 | 0 | 9 | 3 | 0 | 9 |
| | Field Bindweed | 4 | 0 | 9 | 4 | 0 | 9 | 3 | 0 | 9 | 3 | 0 | 9 |
| | Wild Mustard | 4 | 0 | 9 | 4 | 0 | 9 | 2 | 0 | 9 | 2 | 0 | 9 |
| | Morningglory | 3 | 0 | 9 | 2 | 0 | 9 | 2 | 20 | 9 | 1 | 30 | 9 |
| | Soybean | 0 | 100 | 11 | 0 | 100 | 11 | 5 | 0 | 0 | 0 | 100 | 11 |
| | Cocklebur | 3 | 0 | 9 | 2 | 60 | 9 | 2 | 70 | 9 | 2 | 70 | 9 |
| | Wild Buckwheat | 2 | 0 | 9 | 2 | 10 | 9 | 2 | 30 | 9 | 2 | 90 | 9 |
| | Johnsongrass | 2 | 30 | 9 | 2 | 90 | 9 | 2 | 90 | 9 | 1 | 90 | 9 |
| | Purple Nutsedge | | | | | | | | | | 2 | 0 | 9 |

EXPLANATION OF RATING SYSTEM:
V = Vigor;
K = Percent Kill;
F = Footnote
Vigor: 5. No effects
4. Slight injury. Plants have recovered or are expected to fully recover.
3. Moderate to severe injury. Plants are expected to recover with time.
2. Moderate to severe injury. Plants are not expected to recover.
1. Severe injury. Plants are not expected to recover.
Footnotes:
1 = Necrosis
2 = Stunted
3 = Desiccation
4 = Auxillary Growth Stimulation
5 = Nastic responses
6 = Necrotic spots
7 = Growth Stimulation
8 = Defoliant
9 = Chlorosis
10 = Intumescence
11 = Suspected germination failure
12 = Stand may be affected by non-chemical factors

TABLE 2

Postemergence Herbicidal Activity of Certain Hydroxamic Acid Derivatives
Rate of Application - 8.00 kg/ha

| Cpd. of Ex. | Lima Bean | | | Wild Oat | | | Barnyard-grass | | | Green Foxtail | | | Velvet-Leaf | | | Tomato | | | Field Bindweed | | |
|---|---|---|---|---|---|---|---|---|---|---|---|---|---|---|---|---|---|---|---|---|---|
| | V | K | F | V | K | F | V | K | F | V | K | F | V | K | F | V | K | F | V | K | F |
| 1 | 2 | 0 | 9 | 3 | 0 | 9 | 3 | 0 | 9 | 3 | 0 | 9 | 2 | 0 | 9 | 3 | 0 | 9 | 3 | 0 | 9 |
| 2 | 4 | 0 | 6 | 5 | 0 | 0 | 4 | 0 | 1 | 4 | 0 | 1 | 3 | 0 | 9 | 4 | 0 | 9 | 3 | 0 | 9 |
| 3 | 4 | 0 | 2 | 5 | 0 | 0 | 5 | 0 | 0 | 4 | 0 | 9 | 3 | 0 | 9 | 5 | 0 | 0 | 4 | 0 | 9 |
| 4 | 2 | 0 | 9 | 2 | 0 | 9 | 2 | 0 | 9 | 2 | 60 | 9 | 2 | 20 | 9 | 2 | 20 | 9 | 2 | 0 | 9 |
| 5 | 4 | 0 | 6 | 4 | 0 | 9 | 4 | 0 | 9 | 4 | 0 | 9 | 2 | 20 | 9 | 4 | 0 | 9 | 3 | 0 | 9 |
| 6 | 5 | 0 | 0 | 4 | 0 | 1 | 4 | 0 | 1 | 4 | 0 | 1 | 3 | 0 | 9 | 5 | 0 | 0 | 4 | 0 | 9 |
| 7 | 4 | 0 | 6 | 4 | 0 | 9 | 3 | 0 | 9 | 3 | 0 | 9 | 3 | 30 | 9 | 4 | 0 | 9 | 3 | 0 | 9 |
| 8 | 3 | 0 | 9 | 2 | 0 | 9 | 2 | 0 | 9 | 2 | 0 | 9 | 2 | 0 | 9 | 3 | 30 | 9 | 3 | 20 | 9 |
| 9 | 4 | 0 | 2 | 5 | 0 | 0 | 4 | 0 | 3 | 4 | 0 | 3 | 4 | 0 | 9 | 5 | 0 | 0 | 3 | 0 | 9 |
| 10 | 2 | 0 | 9 | 2 | 0 | 9 | 2 | 0 | 9 | 2 | 90 | 9 | 2 | 0 | 9 | 2 | 0 | 9 | 2 | 70 | 9 |
| 11 | 2 | 0 | 9 | 2 | 0 | 9 | 2 | 0 | 9 | 3 | 20 | 9 | 2 | 0 | 9 | 4 | 0 | 9 | 3 | 40 | 9 |
| 12 | 3 | 0 | 9 | 3 | 0 | 9 | 3 | 0 | 9 | 3 | 0 | 9 | 2 | 70 | 9 | 3 | 0 | 9 | — | | |
| 13 | 3 | 0 | 9 | 3 | 0 | 9 | 3 | 0 | 9 | 4 | 0 | 9 | 2 | 90 | 9 | 3 | 0 | 9 | — | | |
| 14 | 3 | 0 | 9 | 3 | 0 | 9 | 3 | 0 | 9 | 4 | 0 | 9 | 2 | 80 | 9 | 3 | 0 | 9 | — | | |
| 16 | 2 | 0 | 9 | 3 | 0 | 9 | 3 | 0 | 9 | 3 | 0 | 9 | 3 | 50 | 9 | 2 | 60 | 9 | 3 | 0 | 9 |
| 17 | 4 | 0 | 1 | 4 | 0 | 1 | 4 | 0 | 1 | 4 | 0 | 1 | 3 | 0 | 9 | 4 | 0 | 1 | 4 | 0 | 1 |
| 18 | 1 | 40 | 9 | 0 | 100 | 0 | 2 | 20 | 9 | 0 | 100 | 0 | 2 | 30 | 9 | 2 | 60 | 9 | 2 | 0 | 9 |
| 19 | 4 | 0 | 1 | 4 | 0 | 1 | 4 | 0 | 1 | 4 | 0 | 1 | 3 | 20 | 9 | 4 | 0 | 9 | 3 | 0 | 9 |
| 20 | 4 | 0 | 0 | 4 | 0 | 9 | 5 | 0 | 0 | 3 | 20 | 2 | 3 | 0 | 9 | 5 | 0 | 0 | 5 | 0 | 0 |
| 21 | 3 | 0 | 9 | 4 | 0 | 1 | 3 | 0 | 9 | 3 | 0 | 9 | 3 | 0 | 9 | 4 | 0 | 9 | 3 | 0 | 9 |
| 22 | 3 | 0 | 9 | 2 | 0 | 9 | 2 | 0 | 9 | 2 | 0 | 9 | 2 | 0 | 9 | 2 | 10 | 9 | 2 | 0 | 9 |
| 23(A) | 2 | 0 | 9 | 2 | 0 | 9 | 2 | 0 | 9 | 3 | 40 | 9 | 2 | 30 | 9 | 2 | 80 | 9 | 3 | 20 | 9 |
| 23(B) | 2 | 0 | 9 | 2 | 0 | 9 | 2 | 0 | 9 | 2 | 0 | 9 | 1 | 50 | 9 | 2 | 20 | 9 | 3 | 60 | 1 |
| 24 | 3 | 0 | 9 | 3 | 0 | 9 | 2 | 0 | 9 | 3 | 0 | 9 | 2 | 0 | 9 | 4 | 0 | 9 | 3 | 0 | 9 |

TABLE 3

Preemergence Herbicidal Activity of Certain Hydroxamic Acid Derivatives
Rate of Application: 2.00 kg/ha (first line)
4.00 kg/ha (second line)

| Cpd. of Ex. | Barnyard-grass | | | Field Bindweed | | | Green Foxtail | | | Lima Bean | | | Soybean | | | Velvet-Leaf | | | Wild Oat | | |
|---|---|---|---|---|---|---|---|---|---|---|---|---|---|---|---|---|---|---|---|---|---|
| | V | K | F | V | K | F | V | K | F | V | K | F | V | K | F | V | K | F | V | K | F |
| 15* | 0 | 100 | 0 | 2 | 20 | 9 | 0 | 100 | 0 | 3 | 0 | 9 | 5 | 0 | 0 | 0 | 100 | 0 | 0 | 100 | 0 |
| | 0 | 100 | 0 | 0 | 100 | 0 | 0 | 100 | 0 | 3 | 50 | 9 | 3 | 40 | 9 | 0 | 100 | 0 | 0 | 100 | 0 |
| 25 | 0 | 100 | 0 | 4 | 0 | 9 | 4 | 80 | 9 | 4 | 0 | 0 | 5 | 0 | 0 | 3 | 80 | 9 | 3 | 80 | 9 |
| | 0 | 100 | 0 | 4 | 0 | 9 | 0 | 100 | 0 | 4 | 20 | 9 | 5 | 0 | 0 | 2 | 95 | 9 | 3 | 95 | 9 |
| 26 | 0 | 100 | 0 | 3 | 60 | 9 | 0 | 100 | 0 | 3 | 0 | 9 | 4 | 0 | 9 | 0 | 100 | 0 | 0 | 100 | 0 |
| | 0 | 100 | 0 | 3 | 100 | 0 | 0 | 100 | 0 | 2 | 80 | 9 | 3 | 0 | 9 | 0 | 100 | 0 | 1 | 95 | 9 |
| 27 | 0 | 100 | 0 | 3 | 50 | 9 | 3 | 80 | 9 | 4 | 0 | 2 | 0 | 100 | 0 | 0 | 100 | 0 | 0 | 100 | 0 |
| | 0 | 100 | 0 | 3 | 90 | 9 | 0 | 100 | 0 | 3 | 60 | 9 | 4 | 0 | 9 | 0 | 100 | 0 | 2 | 95 | 9 |
| 28 | 0 | 100 | 0 | 3 | 0 | 1 | 0 | 100 | 0 | 3 | 0 | 9,4 | 5 | 0 | 0 | 0 | 100 | 0 | 0 | 100 | 0 |
| | 0 | 100 | 0 | 3 | 60 | 1 | 0 | 100 | 0 | 3 | 60 | 9,2 | 4 | 0 | 9 | 0 | 100 | 0 | 0 | 100 | 0 |
| 29 | 2 | 95 | 9,2 | 4 | 0 | 9 | 3 | 40 | 9,2 | 4 | 0 | 0 | 5 | 0 | 0 | 0 | 100 | 0 | 2 | 60 | 9,2 |
| | 0 | 100 | 0 | 4 | 0 | 9 | 2 | 95 | 9,2 | 4 | 0 | 9,2 | 5 | 0 | 0 | 0 | 100 | 0 | 0 | 100 | 0 |
| 30 | 0 | 100 | 0 | 2 | 95 | 9 | 0 | 100 | 0 | 4 | 0 | 2,9 | 4 | 0 | 9 | 0 | 100 | 0 | 0 | 100 | 0 |
| | 0 | 100 | 0 | 1 | 95 | 9 | 0 | 100 | 0 | 3 | 0 | 2,9 | 3 | 20 | 2,9 | 0 | 100 | 0 | 0 | 100 | 0 |
| 31 | 0 | 100 | 0 | 3 | 50 | 9,2 | 0 | 100 | 0 | 2 | 0 | 9,2 | 5 | 0 | 0 | 0 | 100 | 0 | 0 | 100 | 0 |
| | 0 | 100 | 0 | 2 | 95 | 9,2 | 0 | 100 | 0 | 0 | 100 | 0 | 4 | 0 | 9 | 0 | 100 | 0 | 0 | 100 | 0 |
| 32 | 0 | 100 | 0 | 4 | 50 | 9 | 0 | 100 | 0 | 3 | 0 | 2,9 | 5 | 0 | 0 | 4 | 90 | 9 | 3 | 80 | 9 |
| | 0 | 100 | 0 | 3 | 95 | 2,9 | 0 | 100 | 0 | 3 | 0 | 2,9 | 5 | 0 | 0 | 0 | 100 | 0 | 0 | 100 | 0 |
| 33 | 5 | 0 | 0 | 5 | 0 | 0 | 5 | 0 | 0 | 5 | 0 | 0 | 5 | 0 | 0 | 5 | 0 | 0 | 5 | 0 | 0 |
| | 5 | 0 | 0 | 5 | 0 | 0 | 5 | 0 | 0 | 5 | 0 | 0 | 5 | 0 | 0 | 4 | 0 | 1 | 5 | 0 | 0 |
| 34 | 1 | 95 | 9 | 3 | 70 | 9 | 0 | 100 | 0 | 3 | 40 | 9 | 4 | 0 | 9 | 0 | 100 | 0 | 0 | 100 | 0 |
| | 0 | 100 | 0 | 3 | 100 | 0 | 0 | 100 | 0 | 0 | 100 | 0 | 3 | 0 | 9 | 0 | 100 | 0 | 0 | 100 | 0 |
| 35A | 3 | 40 | 9 | 4 | 0 | 9 | 3 | 95 | 9 | 4 | 0 | 9 | 5 | 0 | 0 | 3 | 0 | 9 | 2 | 60 | 9 |
| | 2 | 95 | 9 | 3 | 0 | 9 | 3 | 95 | 9 | 4 | 0 | 9 | 5 | 0 | 0 | 3 | 10 | 9 | 2 | 80 | 9 |
| 35B | 0 | 100 | 0 | 3 | 40 | 9 | 3 | 95 | 9 | 4 | 0 | 9 | 5 | 0 | 0 | 0 | 100 | 0 | 0 | 100 | 0 |
| | 0 | 100 | 0 | 3 | 100 | 0 | 0 | 100 | 0 | 3 | 20 | 2 | 4 | 10 | 9 | 0 | 100 | 0 | 0 | 100 | 0 |
| 36 | 0 | 100 | 0 | 2 | 90 | 9 | 0 | 100 | 0 | 3 | 80 | 11 | 0 | 100 | 11 | 0 | 100 | 0 | 0 | 100 | 0 |
| | 0 | 100 | 0 | 1 | 90 | 9 | 0 | 100 | 0 | 0 | 100 | 0 | 3 | 90 | 11 | 0 | 100 | 0 | 0 | 100 | 0 |
| 37 | 0 | 100 | 0 | 3 | 90 | 9 | 0 | 100 | 0 | 0 | 100 | 11 | 0 | 100 | 11 | 0 | 100 | 0 | 1 | 95 | 9 |
| | 0 | 100 | 0 | 3 | 100 | 0 | 0 | 100 | 0 | 3 | 80 | 11 | 0 | 100 | 11 | 0 | 100 | 0 | 1 | 95 | 9 |
| 38 | 0 | 100 | 0 | 3 | 90 | 9 | 0 | 100 | 0 | 1 | 80 | 11 | 4 | 80 | 11 | 0 | 100 | 0 | 0 | 100 | 0 |
| | 0 | 100 | 0 | 0 | 100 | 0 | 0 | 100 | 0 | 3 | 80 | 11 | 0 | 100 | 11 | 0 | 100 | 0 | 1 | 95 | 9 |
| 39 | 0 | 100 | 0 | 4 | 0 | 9 | 3 | 95 | 9 | 4 | 60 | 11 | 0 | 100 | 11 | 3 | 30 | 9 | 4 | 95 | 9 |
| | 0 | 100 | 0 | 4 | 0 | 9 | 0 | 100 | 0 | 3 | 0 | 9 | 0 | 100 | 11 | 2 | 95 | 9 | 2 | 95 | 9 |
| 40 | 3 | 90 | 9 | 5 | 0 | 0 | 4 | 30 | 9 | 4 | 0 | 9 | 5 | 0 | 0 | 3 | 20 | 9 | 3 | 90 | 9 |
| | 0 | 100 | 0 | 4 | 0 | 9 | 4 | 60 | 9 | 3 | 60 | 9 | 0 | 100 | 11 | 3 | 80 | 9 | 3 | 90 | 9 |
| 41 | 0 | 100 | 0 | 3 | 0 | 9 | 3 | 80 | 9 | 3 | 0 | 9 | 5 | 0 | 0 | 0 | 100 | 0 | 0 | 100 | 0 |
| | 0 | 100 | 0 | 3 | 0 | 9 | 2 | 95 | 9 | 3 | 80 | 9 | 4 | 0 | 9 | 2 | 95 | 9 | 1 | 95 | 9 |
| 42 | 4 | 0 | 9 | 5 | 0 | 0 | 5 | 0 | 0 | 5 | 0 | 0 | 5 | 0 | 0 | 4 | 0 | 9 | 5 | 0 | 0 |

TABLE 3-continued

Preemergence Herbicidal Activity of Certain
Hydroxamic Acid Derivatives
Rate of Application: 2.00 kg/ha (first line)
4.00 kg/ha (second line)

| Cpd. of Ex. | Barnyard-grass | | | Field Bindweed | | | Green Foxtail | | | Lima Bean | | | Soybean | | | Velvet-Leaf | | | Wild Oat | | |
|---|---|---|---|---|---|---|---|---|---|---|---|---|---|---|---|---|---|---|---|---|---|
| | V | K | F | V | K | F | V | K | F | V | K | F | V | K | F | V | K | F | V | K | F |
| | 4 | 0 | 9 | 5 | 0 | 0 | 5 | 0 | 0 | 5 | 0 | 0 | 0 | 100 | 11 | 3 | 0 | 9 | 5 | 0 | 0 |
| 43 | 0 | 100 | 0 | 3 | 20 | 9 | 0 | 100 | 0 | 2 | 60 | 9 | 0 | 100 | 11 | 0 | 100 | 0 | 0 | 100 | 0 |
| | 0 | 100 | 0 | 0 | 100 | 0 | 0 | 100 | 0 | 1 | 80 | 9 | 0 | 100 | 11 | 0 | 100 | 0 | 0 | 100 | 0 |
| 44 | 3 | 90 | 9 | 5 | 0 | 0 | 4 | 0 | 9 | 5 | 0 | 0 | 0 | 100 | 11 | 3 | 0 | 9 | 4 | 0 | 9 |
| | 3 | 90 | 9 | 4 | 0 | 9 | 4 | 0 | 9 | 4 | 0 | 2 | 0 | 100 | 11 | 3 | 20 | 9 | 3 | 80 | 9 |
| 45 | 0 | 100 | 0 | 5 | 0 | 0 | 4 | 0 | 9 | 5 | 0 | 0 | 5 | 0 | 0 | 3 | 50 | 9 | 3 | 0 | 9 |
| | 0 | 100 | 0 | 4 | 0 | 9 | 1 | 90 | 9 | 5 | 0 | 0 | 5 | 0 | 0 | 2 | 50 | 9 | 3 | 20 | 9 |
| 46 | 0 | 100 | 0 | 4 | 0 | 9 | 0 | 100 | 0 | 4 | 0 | 9 | 5 | 0 | 0 | 3 | 60 | 9 | 2 | 90 | 9 |
| | 0 | 100 | 0 | 4 | 0 | 9 | 0 | 100 | 0 | 4 | 0 | 9 | 5 | 0 | 0 | 2 | 95 | 9 | 0 | 100 | 0 |
| 47 | 0 | 100 | 0 | 4 | 0 | 9 | 0 | 100 | 0 | 4 | 0 | 9 | 5 | 0 | 0 | 0 | 100 | 0 | 0 | 100 | 0 |
| | 0 | 100 | 0 | 3 | 0 | 9 | 0 | 100 | 0 | 3 | 0 | 9 | 5 | 0 | 0 | 0 | 100 | 0 | 0 | 100 | 0 |
| 48 | 0 | 100 | 0 | 3 | 0 | 9 | 0 | 100 | 0 | 3 | 0 | 9 | 5 | 0 | 0 | 0 | 100 | 0 | 0 | 100 | 0 |
| | 0 | 100 | 0 | 2 | 90 | 9 | 0 | 100 | 0 | 3 | 80 | 9 | 4 | 0 | 9 | 0 | 100 | 0 | 0 | 100 | 0 |
| 49 | 0 | 100 | 0 | 3 | 50 | 9 | 0 | 100 | 0 | 3 | 0 | 9 | 5 | 0 | 0 | 0 | 100 | 0 | 2 | 80 | 9 |
| | 0 | 100 | 0 | 3 | 0 | 9 | 0 | 100 | 0 | 3 | 0 | 9 | 5 | 0 | 0 | 0 | 100 | 0 | 1 | 90 | 9 |
| 50 | 4 | 0 | 9 | 4 | 0 | 9 | 5 | 0 | 0 | 5 | 0 | 0 | 5 | 0 | 0 | 3 | 0 | 9 | 4 | 0 | 9 |
| | 3 | 0 | 9 | 4 | 0 | 9 | 4 | 0 | 9 | 5 | 0 | 0 | 5 | 0 | 0 | 3 | 10 | 9 | 4 | 0 | 9 |
| 51 | 0 | 100 | 0 | 3 | 60 | 9 | 3 | 90 | 9 | 3 | 0 | 9,4 | 5 | 0 | 0 | 0 | 100 | 0 | 0 | 100 | 0 |
| | 0 | 100 | 0 | 0 | 100 | 0 | 0 | 100 | 0 | 2 | 50 | 9,2 | 5 | 0 | 0 | 0 | 100 | 0 | 0 | 100 | 0 |
| 52 | 0 | 100 | 0 | 0 | 100 | 0 | 3 | 70 | 9 | 3 | 0 | 2,9 | 4 | 50 | 2 | 0 | 100 | 0 | 2 | 95 | 1 |
| | 0 | 100 | 0 | 0 | 100 | 0 | 0 | 100 | 0 | 0 | 100 | 0 | 3 | 60 | 2 | 0 | 100 | 0 | 0 | 100 | 0 |
| 53 | 0 | 100 | 0 | 4 | 0 | 9 | 3 | 90 | 9 | 4 | 0 | 9,4 | 5 | 0 | 0 | 3 | 40 | 9 | 3 | 60 | 9 |
| | 0 | 100 | 0 | 4 | 20 | 9 | 0 | 100 | 0 | 3 | 30 | 9,4 | 5 | 0 | 0 | 1 | 90 | 9 | 0 | 100 | 0 |
| 54 | 0 | 100 | 0 | 4 | 0 | 9 | 3 | 80 | 9 | 3 | 0 | 9,4 | 5 | 0 | 0 | 0 | 100 | 0 | 3 | 40 | 9 |
| | 0 | 100 | 0 | 4 | 0 | 9 | 0 | 100 | 0 | 0 | 100 | 11 | 5 | 0 | 0 | 0 | 100 | 0 | 2 | 90 | 9 |
| 55 | 0 | 100 | 0 | 4 | 20 | 9 | 0 | 100 | 0 | 3 | 60 | 9,2 | 5 | 0 | 0 | 3 | 90 | 9 | 0 | 100 | 0 |
| | 0 | 100 | 0 | 3 | 0 | 9 | 0 | 100 | 0 | 3 | 0 | 9,2 | 5 | 0 | 0 | 0 | 100 | 0 | 0 | 100 | 0 |
| 56 | 0 | 100 | 0 | 4 | 0 | 9 | 0 | 100 | 0 | 4 | 0 | 0 | — | | | 2 | 90 | 9 | 2 | 80 | 9 |
| | 0 | 100 | 0 | 4 | 0 | 9 | 0 | 100 | 0 | 4 | 0 | 9 | — | | | 0 | 100 | 0 | 3 | 70 | 9 |
| 57 | 0 | 100 | 0 | 4 | 20 | 2,9 | 4 | 90 | 0 | 4 | 0 | 2,4 | 4 | 0 | 2 | 0 | 100 | 0 | 2 | 90 | 9 |
| | 0 | 100 | 0 | 3 | 80 | 2,9 | 0 | 100 | 0 | 3 | 40 | 2,4 | 4 | 20 | 2,9 | 2 | 95 | 9 | 0 | 100 | 0 |
| 58 | 0 | 100 | 0 | 3 | 70 | 2,9 | 0 | 100 | 0 | 3 | 0 | 2,4 | 4 | 0 | 0 | 0 | 100 | 0 | 0 | 100 | 0 |
| | 0 | 100 | 0 | 0 | 100 | 0 | 0 | 100 | 0 | 3 | 40 | 2,4 | 4 | 0 | 9 | 0 | 100 | 0 | 0 | 100 | 0 |
| 59 | 0 | 100 | 0 | 3 | 90 | 2,9 | 0 | 100 | 0 | 3 | 0 | 2,4 | 5 | 0 | 0 | 0 | 100 | 0 | 0 | 100 | 0 |
| | 0 | 100 | 0 | 0 | 100 | 0 | 0 | 100 | 0 | 3 | 0 | 2,4 | 4 | 0 | 9 | 0 | 100 | 0 | 0 | 100 | 0 |
| 60 | 0 | 100 | 0 | 3 | 95 | 9 | 0 | 100 | 0 | 3 | 50 | 2,4 | 5 | 0 | 0 | 0 | 100 | 0 | 0 | 100 | 0 |
| | 0 | 100 | 0 | 3 | 95 | 2,9 | 0 | 100 | 0 | 3 | 50 | 2,4 | 5 | 0 | 0 | 0 | 100 | 0 | 0 | 100 | 0 |
| 61 | 0 | 100 | 0 | 0 | 100 | 0 | 0 | 100 | 0 | 3 | 30 | 2,4 | 5 | 0 | 0 | 0 | 100 | 0 | 0 | 100 | 0 |
| | 0 | 100 | 0 | 2 | 95 | 9 | 0 | 100 | 0 | 3 | 30 | 2,4 | 4 | 0 | 9 | 0 | 100 | 0 | 0 | 100 | 0 |
| 62 | 0 | 100 | 0 | 3 | 100 | 0 | 0 | 100 | 0 | 3 | 20 | 2,4 | 5 | 0 | 0 | 0 | 100 | 0 | 0 | 100 | 0 |
| | 0 | 100 | 0 | 2 | 90 | 2,9 | 0 | 100 | 0 | 2 | 30 | 2,4 | 3 | 0 | 9 | 0 | 100 | 0 | 0 | 100 | 0 |
| 63 | 4 | 0 | 2,9 | 5 | 0 | 0 | 4 | 0 | 9 | 4 | 0 | 0 | 5 | 0 | 0 | 3 | 30 | 9 | — | | |
| | 3 | 0 | 2,9 | 4 | 0 | 9 | 4 | 0 | 2,9 | 4 | 0 | 9 | 5 | 0 | 0 | 3 | 60 | 2,9 | — | | |
| 64 | 0 | 100 | 0 | 3 | 0 | 9 | 3 | 95 | 2 | 4 | 0 | 9 | 4 | 0 | 9 | 0 | 100 | 0 | 3 | 95 | 9 |
| | 0 | 100 | 0 | 0 | 100 | 0 | 0 | 100 | 0 | 3 | 0 | 2,4 | 3 | 0 | 9 | 0 | 100 | 0 | 0 | 100 | 0 |
| 65 | 0 | 100 | 0 | 3 | 80 | 9 | 3 | 95 | 2,9 | 4 | 0 | 2,4 | 4 | 0 | 9 | 0 | 100 | 0 | 3 | 95 | 9 |
| | 0 | 100 | 0 | 3 | 80 | 2,9 | 3 | 95 | 2,9 | 3 | 0 | 2,4 | 3 | 0 | 9 | 0 | 100 | 0 | 0 | 100 | 0 |
| 66 | 0 | 100 | 0 | 3 | 50 | 9 | 0 | 100 | 0 | 4 | 0 | 2,4 | 5 | 0 | 0 | 0 | 100 | 0 | 0 | 100 | 0 |
| | 0 | 100 | 0 | 3 | 60 | 9 | 0 | 100 | 0 | 3 | 0 | 2,4 | 3 | 0 | 9 | 0 | 100 | 0 | 0 | 100 | 0 |
| 67 | 4 | 0 | 9 | 4 | 0 | 9 | 4 | 0 | 9 | 4 | 0 | 0 | 5 | 0 | 0 | 3 | 30 | 9 | 5 | 0 | 0 |
| | 3 | 80 | 2,9 | 3 | 0 | 9 | 4 | 0 | 2,9 | 4 | 0 | 6 | 5 | 0 | 0 | 2 | 80 | 9 | 4 | 0 | 9 |
| 68 | 2 | 95 | 2,9 | 4 | 0 | 9 | 3 | 90 | 2,9 | 5 | 0 | 0 | 5 | 0 | 0 | 3 | 95 | 9 | 3 | 70 | 9 |
| | 0 | 100 | 0 | 4 | 0 | 9 | 3 | 95 | 2,9 | 4 | 0 | 9 | 5 | 0 | 0 | 2 | 95 | 9 | 2 | 95 | 9 |
| 69 | 5 | 0 | 0 | 5 | 0 | 0 | 5 | 0 | 0 | 5 | 0 | 0 | 5 | 0 | 0 | 5 | 0 | 0 | 4 | 95 | 11 |
| | 5 | 0 | 0 | 5 | 0 | 0 | 5 | 0 | 0 | 5 | 0 | 0 | 5 | 0 | 0 | 5 | 0 | 0 | 4 | 95 | 11 |
| 70 | 5 | 0 | 0 | 5 | 0 | 0 | 5 | 0 | 0 | 5 | 0 | 0 | 5 | 0 | 0 | 5 | 0 | 0 | 5 | 0 | 0 |
| | 5 | 0 | 0 | 5 | 0 | 0 | 5 | 0 | 0 | 5 | 0 | 0 | 5 | 0 | 0 | 5 | 0 | 0 | 5 | 0 | 0 |
| 71 | 0 | 100 | 0 | 4 | 0 | 9 | 0 | 100 | 0 | 4 | 0 | 9 | 5 | 0 | 0 | 0 | 100 | 0 | 3 | 30 | 9 |
| | 0 | 100 | 0 | 4 | 90 | 9 | 0 | 100 | 0 | 3 | 20 | 9 | 5 | 0 | 0 | 0 | 100 | 0 | 0 | 100 | 0 |
| 72 | 0 | 100 | 0 | 4 | 0 | 9 | 3 | 95 | 2 | 40 | 9 | 5 | 0 | 0 | 3 | 40 | 9 | 3 | 80 | 9 |
| | 0 | 100 | 0 | 4 | 60 | 9 | 3 | 95 | 2 | 3 | 0 | 9 | 5 | 0 | 0 | 3 | 90 | 2 | 3 | 95 | 2 |
| 73 | 0 | 100 | 0 | 4 | 0 | 9 | 0 | 100 | 0 | 4 | 0 | 9 | 5 | 0 | 0 | 3 | 90 | 9 | 3 | 90 | 9 |
| | 0 | 100 | 0 | 4 | 20 | 9 | 0 | 100 | 0 | 4 | 0 | 2,9 | 5 | 0 | 0 | 0 | 100 | 0 | 0 | 100 | 0 |
| 74 | 0 | 100 | 0 | 4 | 0 | 9 | 4 | 0 | 9 | 4 | 0 | 9 | 5 | 0 | 0 | 3 | 0 | 9 | 4 | 40 | 9 |
| | 0 | 100 | 0 | 4 | 0 | 9 | 4 | 0 | 9 | 4 | 0 | 9 | 5 | 0 | 0 | 3 | 0 | 9 | 3 | 40 | 9 |
| 75 | 3 | 95 | 9 | 4 | 0 | 9 | 4 | 0 | 9 | 3 | 0 | 2,4 | 5 | 0 | 0 | 3 | 0 | 9 | 3 | 20 | 9 |
| | 3 | 95 | 9 | 3 | 0 | 9 | 4 | 20 | 9 | 3 | 0 | 2,4 | 4 | 0 | 9 | 3 | 90 | 9 | 3 | 60 | 9 |
| 76 | 0 | 100 | 0 | 4 | 0 | 9 | 3 | 95 | 2,9 | 3 | 0 | 2,4 | 5 | 0 | 3 | 90 | 2,9 | 3 | 20 | 9 |
| | 0 | 100 | 0 | 3 | 0 | 9 | 0 | 100 | 0 | 3 | 0 | 2,4 | 3 | 0 | 2,9 | 2 | 90 | 2 | 3 | 40 | 9 |
| 77 | 0 | 100 | 0 | 4 | 0 | 9 | 0 | 100 | 0 | 5 | 0 | 0 | 5 | 0 | 0 | 3 | 80 | 2,9 | 5 | 0 | 0 |
| | 0 | 100 | 0 | 4 | 0 | 9 | 0 | 100 | 0 | 4 | 0 | 0 | 5 | 0 | 0 | 0 | 100 | 0 | 4 | 0 | 9 |
| 78 | 0 | 100 | 0 | 4 | 0 | 9 | 0 | 100 | 0 | 5 | 0 | 0 | 5 | 0 | 0 | 0 | 100 | 0 | 5 | 0 | 0 |
| | — | | | — | | | — | | | — | | | — | | | — | | | — | | |
| 79 | 4 | 0 | 1 | 5 | 0 | 0 | 4 | 0 | 1 | 5 | 0 | 0 | 5 | 0 | 0 | 5 | 0 | 0 | 4 | 0 | 1 |

TABLE 3-continued
Preemergence Herbicidal Activity of Certain Hydroxamic Acid Derivatives
Rate of Application: 2.00 kg/ha (first line) 4.00 kg/ha (second line)

| Cpd. of Ex. | Barnyard-grass | | | Field Bindweed | | | Green Foxtail | | | Lima Bean | | | Soybean | | | Velvet-Leaf | | | Wild Oat | | |
|---|---|---|---|---|---|---|---|---|---|---|---|---|---|---|---|---|---|---|---|---|---|
| | V | K | F | V | K | F | V | K | F | V | K | F | V | K | F | V | K | F | V | K | F |
| | 3 | 10 | 9 | 4 | 0 | 9 | 3 | 0 | 9 | 4 | 0 | 9 | 5 | 0 | 0 | 4 | 0 | 9 | 4 | 0 | 9 |
| 80 | 0 | 100 | 0 | 4 | 0 | 9 | 0 | 100 | 0 | 4 | 0 | 0 | 5 | 0 | 0 | 1 | 95 | 9 | 3 | 40 | 2,9 |
| | 0 | 100 | 0 | 3 | 30 | 9 | 0 | 100 | 0 | 4 | 0 | 9 | 5 | 0 | 0 | 0 | 100 | 0 | 0 | 100 | 0 |
| 81 | 0 | 100 | 0 | 3 | 0 | 2,9 | 0 | 100 | 0 | 5 | 0 | 0 | 5 | 0 | 0 | 4 | 0 | 2,9 | 3 | 80 | 2,9 |
| | 0 | 100 | 0 | 2 | 20 | 2,9 | 0 | 100 | 0 | 4 | 0 | 0 | 3 | 0 | 2,9 | 0 | 100 | 0 | 2 | 90 | 2,9 |
| 82 | 0 | 100 | 0 | 4 | 0 | 9 | 3 | 95 | 9 | 5 | 0 | 0 | 5 | 0 | 0 | 3 | 40 | 9 | 4 | 0 | 9 |
| | 0 | 100 | 0 | 4 | 0 | 9 | 0 | 100 | 9 | 5 | 0 | 0 | 5 | 0 | 0 | 0 | 100 | 0 | 4 | 0 | 9 |
| 83 | 4 | 10 | 9 | 4 | 0 | 9 | 5 | 0 | 0 | 5 | 0 | 0 | 5 | 0 | 0 | 3 | 0 | 9 | 4 | 0 | 9 |
| | 3 | 90 | 9 | 3 | 0 | 9 | 4 | 0 | 9 | 5 | 0 | 0 | 5 | 0 | 0 | 3 | 0 | 9 | 4 | 0 | 9 |
| 84 | 0 | 100 | 0 | 3 | 50 | 9 | 0 | 100 | 0 | 3 | 80 | 9 | 0 | 100 | 11 | 0 | 100 | 0 | 1 | 95 | 9 |
| | 0 | 100 | 0 | 3 | 80 | 9 | 0 | 100 | 0 | 1 | 50 | 9 | 2 | 0 | 9 | 0 | 100 | 0 | 1 | 95 | 9 |
| 85 | 0 | 100 | 0 | 5 | 0 | 0 | 4 | 40 | 9 | 4 | 0 | 2 | 5 | 0 | 0 | 30 | 9 | 1 | 95 | 9 | |
| | 0 | 100 | 0 | 4 | 40 | 9 | 4 | 80 | 9 | 4 | 80 | 11 | 5 | 0 | 0 | 3 | 30 | 9 | 0 | 100 | 0 |
| 86 | 0 | 100 | 0 | 4 | 0 | 9 | 4 | 0 | 9 | 4 | 0 | 9 | 5 | 0 | 0 | 4 | 20 | 9 | 3 | 80 | 9 |
| | 4 | 95 | 9 | 4 | 0 | 9 | 4 | 20 | 9 | 3 | 20 | 9 | 4 | 0 | 9 | 0 | 100 | 0 | 3 | 90 | 9 |
| 87 | 0 | 100 | 0 | 3 | 50 | 9 | 0 | 100 | 0 | 3 | 0 | 9 | 5 | 0 | 0 | 2 | 0 | 9 | 3 | 10 | 9 |
| | 0 | 100 | 0 | 0 | 100 | 0 | 0 | 100 | 0 | 2 | 70 | 1 | 4 | 0 | 1 | 1 | 95 | 9 | 0 | 100 | 0 |
| 88 | 0 | 100 | 0 | 40 | 9 | 0 | 100 | 0 | 4 | 0 | 2,4 | 4 | 0 | 9 | 0 | 100 | 0 | 0 | 100 | 0 | |
| | 0 | 100 | 0 | 3 | 0 | 2,9 | 0 | 100 | 0 | 1 | 80 | 1 | 4 | 0 | 9 | 0 | 100 | 0 | 0 | 100 | 0 |
| 89 | 0 | 100 | 0 | 4 | 60 | 2,9 | 0 | 100 | 0 | 3 | 50 | 2,4 | 4 | 0 | 9 | 0 | 100 | 0 | 0 | 100 | 0 |
| | 0 | 100 | 0 | 3 | 90 | 2,9 | 0 | 100 | 0 | 2 | 50 | 2,4 | 2 | 0 | 2,9 | 0 | 100 | 0 | 0 | 100 | 0 |
| 90 | 0 | 100 | 0 | 0 | 100 | 0 | 0 | 100 | 0 | 2 | 20 | 2,4 | 3 | 10 | 9 | 0 | 100 | 0 | 0 | 100 | 0 |
| | 0 | 100 | 0 | 0 | 100 | 0 | 0 | 100 | 0 | 0 | 100 | 0 | 2 | 30 | 2,9 | 0 | 100 | 0 | 0 | 100 | 0 |
| 91 | 4 | 70 | 9 | 4 | 0 | 9 | 4 | 0 | 9 | 4 | 0 | 9 | 5 | 0 | 0 | 3 | 95 | 9 | 4 | 0 | 9 |
| | 3 | 95 | 2,9 | 5 | 0 | 0 | 4 | 30 | 2,9 | 3 | 0 | 2,9 | 5 | 0 | 0 | 2 | 90 | 9 | 3 | 0 | 9 |
| 92 | 5 | 0 | 0 | 4 | 0 | 9 | 5 | 0 | 0 | 5 | 0 | 0 | 5 | 0 | 0 | 4 | 0 | 9 | 4 | 0 | 9 |
| | 3 | 0 | 9 | 4 | 0 | 9 | 4 | 0 | 9 | 5 | 0 | 0 | 5 | 0 | 3 | 3 | 0 | 9 | 4 | 0 | 9 |
| 93 | 0 | 100 | 0 | 5 | 0 | 0 | 3 | 60 | 9,2 | 4 | 0 | 9 | 5 | 0 | 0 | 3 | 60 | 9,2 | 4 | 65 | 9 |
| | 0 | 100 | 0 | 4 | 0 | 9 | 0 | 100 | 0 | 4 | 0 | 9 | 5 | 0 | 0 | 0 | 100 | 0 | 0 | 100 | 0 |
| 94 | 4 | 25 | 9 | 5 | 0 | 0 | 5 | 0 | 0 | 50 | 0 | 5 | 0 | 0 | 4 | 0 | 9 | 4 | 0 | 9 | |
| | 2 | 95 | 9,2 | 4 | 0 | 9 | 4 | 10 | 9,2 | 5 | 0 | 0 | 5 | 0 | 0 | 3 | 25 | 9,2 | 3 | 65 | 9,2 |
| 95 | 0 | 100 | 0 | 4 | 0 | 9 | 0 | 100 | 0 | 4 | 0 | 9 | 5 | 0 | 0 | 2 | 95 | 9 | 0 | 100 | 0 |
| | 0 | 100 | 0 | 3 | 0 | 9,2 | 0 | 100 | 0 | 2 | 95 | 9,2 | 4 | 0 | 9 | 0 | 100 | 0 | 0 | 100 | 0 |
| 96 | 0 | 100 | 0 | 4 | 0 | 9 | 0 | 100 | 0 | 4 | 0 | 9 | 5 | 0 | 0 | 3 | 0 | 9 | 3 | 60 | 9,2 |
| | 0 | 100 | 0 | 4 | 0 | 9 | 0 | 100 | 0 | 3 | 0 | 9,2 | 4 | 0 | 9 | 3 | 0 | 9 | 0 | 100 | 0 |
| 97 | 2 | 95 | 9,2 | 5 | 0 | 0 | 3 | 0 | 9,2 | 4 | 0 | 2 | 5 | 0 | 0 | 4 | 10 | 9,2 | 4 | 0 | 9 |
| | 2 | 95 | 9,2 | 5 | 0 | 0 | 2 | 60 | 9,2 | 4 | 0 | 2 | 5 | 0 | 0 | 3 | 20 | 9,2 | 3 | 50 | 9,2 |
| 98 | 3 | 85 | 9,2 | 5 | 0 | 0 | 0 | 100 | 0 | 4 | 0 | 0 | 5 | 0 | 0 | 4 | 0 | 9 | 4 | 85 | 9 |
| | 2 | 95 | 9,2 | 4 | 0 | 9 | 0 | 100 | 0 | 3 | 0 | 9,2 | 5 | 0 | 4 | 60 | 9,2 | 2 | 95 | 9,2 | |
| 99 | 0 | 100 | 0 | 4 | 0 | 9 | 3 | 70 | 9,2 | 4 | 0 | 9 | 5 | 0 | 0 | 4 | 20 | 9,2 | 3 | 60 | 9,2 |
| | 3 | 75 | 9,2 | 4 | 0 | 9 | 0 | 100 | 0 | 4 | 0 | 9 | 5 | 0 | 0 | 0 | 100 | 0 | 0 | 100 | 0 |
| 100* | 4 | 50 | 9 | 5 | 0 | 0 | 5 | 0 | 0 | 5 | 0 | 0 | 5 | 0 | 0 | 3 | 40 | 9,2 | 3 | 75 | 9,2 |
| | 0 | 100 | 0 | 5 | 0 | 0 | 4 | 0 | 2 | 5 | 0 | 0 | 5 | 0 | 0 | 2 | 95 | 9,2 | 3 | 95 | 9 |
| 101 | 4 | 40 | 9,2 | 5 | 0 | 4 | 20 | 9,2 | 4 | 0 | 2 | 5 | 0 | 0 | 2 | 60 | 9,2 | 4 | 50 | 9,2 | |
| | 2 | 90 | 9,2 | 4 | 0 | 9 | 2 | 95 | 9,2 | 4 | 0 | 9,2 | 5 | 0 | 0 | 2 | 80 | 9,2 | 4 | 75 | 9,2 |
| 102 | 0 | 100 | 0 | 4 | 0 | 9 | 0 | 100 | 0 | 5 | 0 | 0 | 5 | 0 | 0 | 2 | 95 | 9,2 | 2 | 90 | 9,2 |
| | 0 | 100 | 0 | 3 | 0 | 9,2 | 0 | 100 | 0 | 3 | 0 | 9 | 4 | 0 | 9 | 0 | 100 | 0 | 0 | 100 | 0 |
| 103 | 4 | 20 | 9 | 5 | 0 | 0 | 5 | 0 | 0 | 5 | 0 | 0 | 5 | 0 | 0 | 4 | 0 | 9 | 4 | 30 | 1 |
| | 0 | 100 | 0 | 5 | 0 | 0 | 4 | 0 | 9,2 | 5 | 0 | 0 | 5 | 0 | 0 | 3 | 60 | 9,2 | 4 | 50 | 1 |
| 104 | 0 | 100 | 0 | 4 | 0 | 9 | 4 | 80 | 9 | 5 | 0 | 0 | 5 | 0 | 0 | 3 | 0 | 9 | 3 | 75 | 9 |
| | 0 | 100 | 0 | 4 | 0 | 0 | 0 | 100 | 9 | 5 | 0 | 0 | 5 | 0 | 0 | 3 | 0 | 9 | 2 | 95 | 9 |
| 105 | 0 | 100 | 0 | 4 | 50 | 9 | 0 | 100 | 0 | 4 | 0 | 2,9 | 5 | 0 | 0 | 2 | 90 | 9 | — | | |
| | 0 | 100 | 0 | 3 | 80 | 2,9 | 0 | 100 | 0 | 3 | 20 | 2,9 | 3 | 0 | 9 | 0 | 100 | 0 | — | | |
| 106 | 0 | 100 | 0 | 4 | 30 | 9 | 0 | 100 | 0 | 3 | 0 | 9,2 | 5 | 0 | 0 | 2 | 40 | 9 | 3 | 90 | 9 |
| | 0 | 100 | 0 | 4 | 50 | 9 | 3 | 95 | 9 | 3 | 60 | 9,4 | 5 | 0 | 0 | 3 | 95 | 9 | 0 | 100 | 0 |

*Rate of application: 1.00 kg/ha (first line) 2.00 kg/ha (second line)

I claim:
1. A compound of the formula

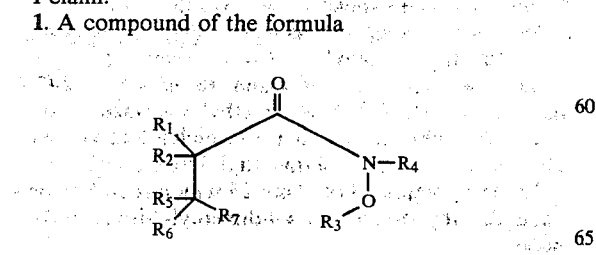

in which
$R_1$ and $R_2$ are independently methyl or ethyl;
$R_3$ is hydrogen, tetrahydropyranyl, tert-butyl-dimethylsilyl, arylsulfonyl, or

in which $R_8$ is $C_1$–$C_6$ alkyl, haloalkyl, phenyl, methylphenyl, nitrophenyl, chlorophenyl, trifluoromethylphenyl, alkylamino, phenylamino, methylphenylamino, methoxyphenylamino, halophenylamino, trifluoromethylphenylamino, alkoxy, haloalkoxy, phenoxy, dichlorophenoxyalkyl, alkylthio, or $R_3$ with $R_7$ comprises a single carbon-oxygen bond, forming a ring structure;
$R_4$ is

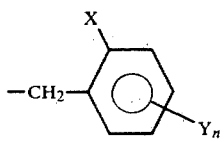

in which X is hydrogen, methyl, chlorine, bromine, fluorine, iodine, Y is chlorine, bromine, fluorine, cyano, methoxy, 4,5-methylenedioxy, and n is 0, 1, or 2;

$R_5$ is hydrogen, chlorine, bromine, phenylamino, or —$OR_9$ in which $R_9$ is hydrogen, alkyl, alkenyl, alkynyl, alkoxyalkyl up to 6 carbons, benzyl, $C_2$–$C_4$ acyl, haloacyl, benzoyl, alkylcarbamoyl, phenylcarbamoyl, with the proviso that when $R_3$ with $R_7$ does not comprise a single carbon-oxygen bond, $R_5$ is limited to hydrogen or chlorine.

$R_6$ is hydrogen;

$R_7$ is hydrogen, chlorine, bromine, methylthio, acetoxy, benzoyloxy, or $R_7$ with $R_3$ comprises a single carbon-oxygen bond, forming a ring structure.

2. The compound of claim 1 in which $R_1$ and $R_2$ are methyl; $R_4$ is

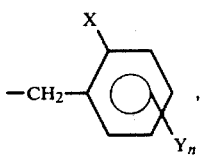

in which X is chlorine, bromine, fluorine, Y is chlorine and fluorine in the 4- or 5-position and bromine in the 4-position when n is 1 and chlorine in the 4- and 5-position or fluorine in the 4- and 5-positions when n is 2.

3. The compound of claim 2 in which $R_3$ is hydrogen, tetrahydropyranyl, tert-butyl-dimethylsilyl,

in which $R_8$ is $C_1$–$C_3$ alkyl, chloromethyl, 1-chloroethyl, phenyl, trifluoromethylphenyl, methylamino, phenylamino, chlorophenylamino, fluorophenylamino, methoxyphenylamino, trifluoromethylphenylamino, $C_1$–$C_2$ alkoxy, chloroalkoxy, phenoxy, dichlorophenoxymethyl; $R_7$ is chlorine, bromine, benzoyloxy.

4. The compound of claim 2 in which $R_3$ and $R_7$ comprise a single carbon-oxygen bond, forming a ring structure.

5. The compound of claim 4 in which $R_5$ is hydrogen, chlorine, or $OR_9$ in which $R_9$ is hydrogen, methyl, ethyl, isopropyl, sec-butyl, cyclopropylmethyl, 2-propenyl, 2-butenyl, 2-propynyl, acetyl, chloroacetyl, benzoyl.

6. The compound of claim 1 which is 3-chloro-N-(2-chlorophenyl)methyl-N-hydroxy-2,2-dimethylpropanamide.

7. The compound of claim 1 which is N-(2-bromophenyl)methyl-3-chloro-N-hydroxy-2,2-dimethylpropanamide.

8. The compound of claim 1 which is 3-chloro-N-(2,4-dichlorophenyl)methyl-N-hydroxy-2,2-dimethylpropanamide.

9. The compound of claim 1 which is 3-bromo-N-(2-chlorophenyl)methyl-N-hydroxy-2,2-dimethylpropanamide.

10. The compound of claim 1 which is N-benzoyloxy-3-chloro-N-(2-chlorophenyl)methyl-2,2-dimethylpropanamide.

11. The compound of claim 1 which is N-acetoxy-3-chloro-N-(2-chlorophenyl)methyl-2,2-dimethylpropanamide.

12. The compound of claim 1 which is N-(chloroacetoxy)-3-chloro-N-(2-chlorophenyl)methyl-2,2-dimethylpropanamide.

13. The compound of claim 1 in which is 3,3-dichloro-N-(2-chlorophenyl)methyl-N-hydroxy-2,2-dimethylpropanamide.

14. The compound of claim 1 which is 3-chloro-N-[(2,4-dichlorophenoxy)acetoxy]-N-[(2-chlorophenyl)methyl]-2,2-dimethylpropanamide.

15. A compound of the formula

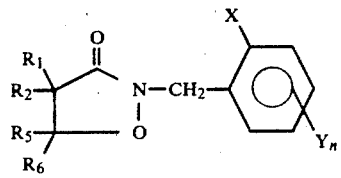

in which $R_1$ and $R_2$ are independently methyl or ethyl;

$R_5$ is hydrogen, chlorine, bromine, phenylamino, or —$OR_9$ in which $R_9$ is hydrogen, alkyl, alkenyl, alkynyl, alkoxyalkyl up to 6 carbons, benzyl, $C_2$–$C_4$ acyl, haloacyl, benzoyl, alkylcarbamoyl, phenylcarbamoyl;

$R_6$ is hydrogen;

X is hydrogen, methyl chlorine, bromine, fluorine, iodine;

Y is chlorine, bromine, fluorine, cyano, methoxy, 4,5-methylenedioxy;

n is 0, 1, or 2.

16. The compound of claim 15 in which $R_1$ and $R_2$ are methyl; X is chlorine, bromine, fluorine; Y is chlorine and fluorine in the 4- or 5-position and bromine in the 4-position when n is 1, and chlorine in the 4- and 5-positions or fluorine in the 4- and 5-positions when n is 2.

17. The compound of claim 16 in which $R_5$ is hydrogen, chlorine, or $OR_9$ in which $R_9$ is hydrogen, methyl, ethyl, isopropyl, sec-butyl, cyclopropylmethyl, 2-propenyl, 2-butenyl, 2-propynyl, acetyl, chlorinated acetyl, benzoyl.

18. The compound of claim 15 which is 2-(2-chlorophenyl)methyl-4,4-dimethyl-3-isoxazolidinone.

19. The compound of claim 15 which is 2-(2-bromophenyl)methyl-4,4-dimethyl-3-isoxazolidinone.

20. The compound of claim 15 which is 2-(2,4-dichlorophenyl)methyl-4,4-dimethyl-3-isoxazolidinone.

21. The compound of claim 15 which is 5-chloro-2-(2-chlorophenyl)methyl-4,4-dimethyl-3-isoxazolidinone.

22. The compound of claim 15 which is 2-(2-chlorophenyl)methyl-5-methoxy-4,4-dimethyl-3-isoxazolidinone.

23. The compound of claim 15 which is 2-(2-chlorophenyl)methyl-5-ethoxy-4,4-dimethyl-3-isoxazolidinone.

24. The compound of claim 15 which is 2-(2-chlorophenyl)methyl-5-hydroxy-4,4-dimethyl-3-isoxazolidinone.

25. The compound of claim 15 which is 2-(2-chloro-4-fluorophenyl)methyl-4,4-dimethyl-3-isoxazolidinone.

26. The compound of claim 15 which is 2-(2-chloro-5-fluorophenyl)methyl-4,4-dimethyl-3-isoxazolidinone.

27. An herbicidal composition comprising an herbicidally effective amount of a compound of claim 1 in admixture with at least one agriculturally acceptable carrier and at least one surface active agent.

28. A method of controlling undesired plant growth which comprises applying to the locus to be protected an herbicidally effective amount of a compound of claim 1.

29. The method of claim 28 in which the locus to be protected is planted with soybeans or to be planted with soybeans.

30. The method of claim 28 in which the locus to be protected is planted with potatoes or to be planted with potatoes.

31. The method of claim 28 in which the compound is the compound of claim 6, 7, 8, 9, 10, 11, 12, 13, or 14.

32. An herbicidal composition comprising an herbicidally effective amount of a compound of claim 15 in admixture with at least one agriculturally acceptable carrier and at least one surface active agent.

33. A method of controlling undesired plant growth which comprises applying to the locus to be protected an herbicidally effective amount of a compound of claim 15.

34. The method of claim 33 in which the locus to be protected is planted with soybeans or to be planted with soybeans.

35. The method of claim 33 in which the locus to be protected is planted with potatoes or to be planted with potatoes.

36. The method of claim 33 in which the compound is the compound of claim 18, 19, 20, 21, 22, 23, 24, 25 or 26.

* * * * *